US008691588B2

(12) United States Patent
Park et al.

(10) Patent No.: US 8,691,588 B2
(45) Date of Patent: Apr. 8, 2014

(54) NANOFILTER DEVICES USING ELASTOMERIC MICRO TO NANOCHANNEL INTERFACES AND METHODS BASED THEREON

(75) Inventors: Seung-min Park, Albany, CA (US); Yun Suk Huh, Daejeon (KR); David Erickson, Ithaca, NY (US); Harold G. Craighead, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/391,508

(22) PCT Filed: Aug. 20, 2010

(86) PCT No.: PCT/US2010/046170
§ 371 (c)(1),
(2), (4) Date: Apr. 17, 2012

(87) PCT Pub. No.: WO2011/022650
PCT Pub. Date: Feb. 24, 2011

(65) Prior Publication Data
US 2012/0196376 A1 Aug. 2, 2012

Related U.S. Application Data

(60) Provisional application No. 61/236,074, filed on Aug. 21, 2009.

(51) Int. Cl.
*B29C 43/44* (2006.01)
*B29C 43/00* (2006.01)
*B29C 59/02* (2006.01)

(52) U.S. Cl.
USPC .................. 436/94; 436/93; 436/91

(58) Field of Classification Search
USPC .................................. 436/94, 93, 91
See application file for complete search history.

(56) References Cited

U.S. PATENT DOCUMENTS

| | | | |
|---|---|---|---|
| 2002/0072243 | A1 | 6/2002 | Craighead et al. |
| 2003/0040173 | A1 | 2/2003 | Fonash et al. |
| 2003/0203271 | A1 | 10/2003 | Morse et al. |
| 2003/0209314 | A1 | 11/2003 | Guo et al. |
| 2004/0209392 | A1 | 10/2004 | Craighead et al. |
| 2004/0211054 | A1 | 10/2004 | Morse et al. |

(Continued)

OTHER PUBLICATIONS

Huh, D. et al., Tuneable elastomeric nanochannels for nanofluidic manipulation, Nature, Nov. 6, Jun. 2007, pp. 424-428.*

*Primary Examiner* — Christine T Mui
(74) *Attorney, Agent, or Firm* — William Greener; Alex P. Szecsy; Bond, Schoeneck & King PLLC

(57) ABSTRACT

A method is provided for fabricating a nanochannel. The method comprises providing a microchannel and controlling collapse of the microchannel so that it collapses to form a nanochannel of desired dimensions. The method employs a collapsible, flexible material such as the elastomer polydimethylsiloxane (PDMS) to form the nanochannel. A master is provided that is configured to have geometric conditions that promote a desired frequency of microchannel collapse. A collapsible material having a stiffness that also promotes a desired frequency of microchannel collapse is molded on the master. The molded collapsible material is removed from the master and bonded to a base, thereby forming the microchannel, which then collapses (or is collapsed) to form the nanochannel of desired dimensions. Nanofluidic and microfluidic devices comprising complex nanochannel structures and micro to nanochannel transitions are also provided.

29 Claims, 8 Drawing Sheets

(56) References Cited

U.S. PATENT DOCUMENTS

Figure 1B:
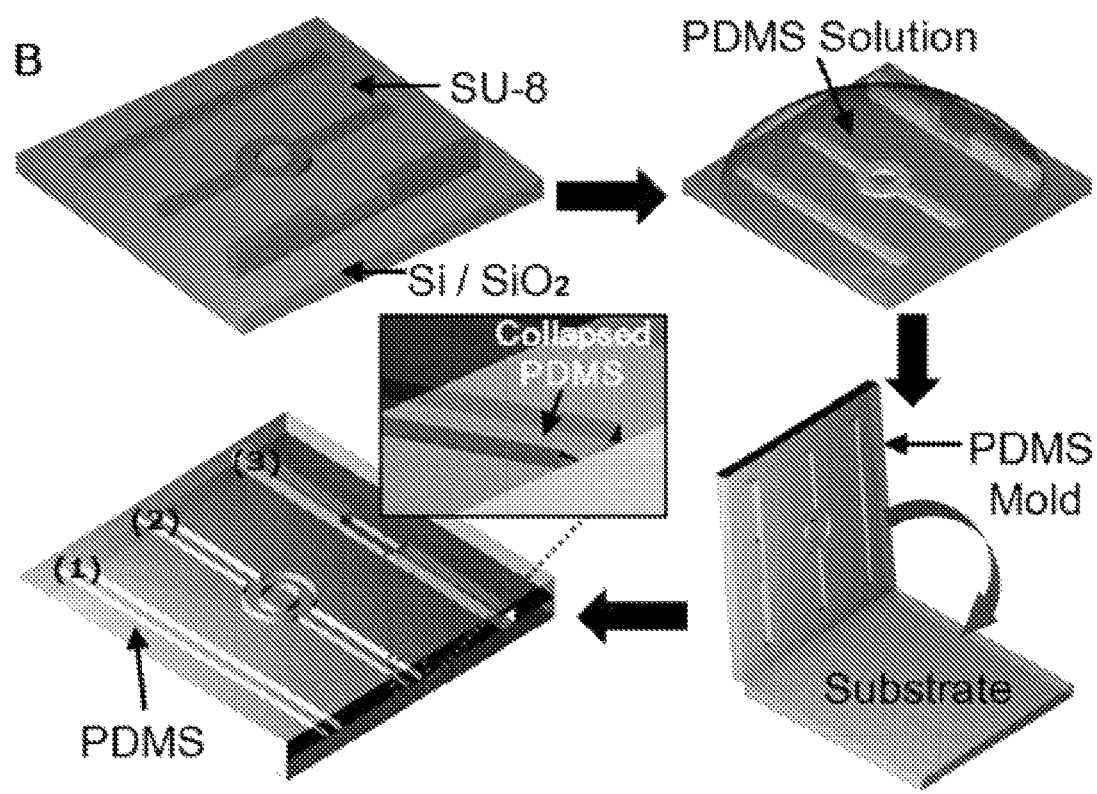

| | | |
|---|---|---|
| 2006/0257627 A1 | 11/2006 | Shim et al. |
| 2006/0275806 A1 | 12/2006 | Schwartz et al. |
| 2006/0286488 A1 | 12/2006 | Rogers et al. |
| 2007/0161028 A1 | 7/2007 | Schwartz et al. |
| 2008/0213821 A1 | 9/2008 | Liu et al. |
| 2008/0242556 A1 | 10/2008 | Cao et al. |
| 2009/0053471 A1 | 2/2009 | Hamedi et al. |

\* cited by examiner

A
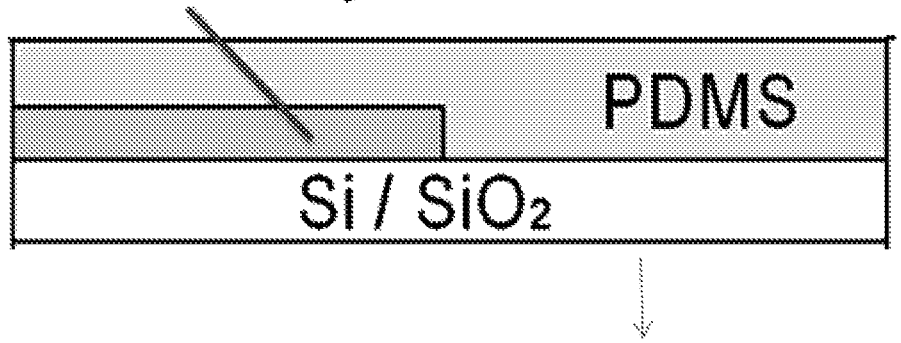
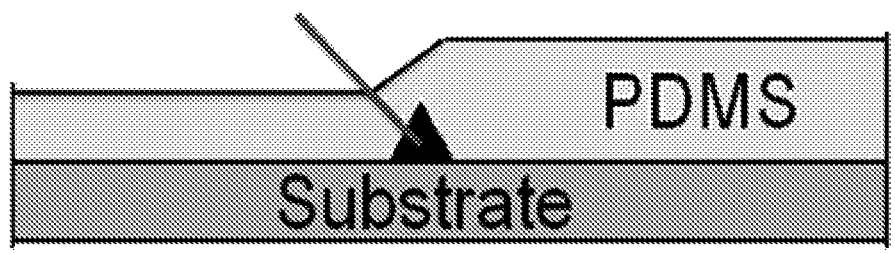
FIG. 1A

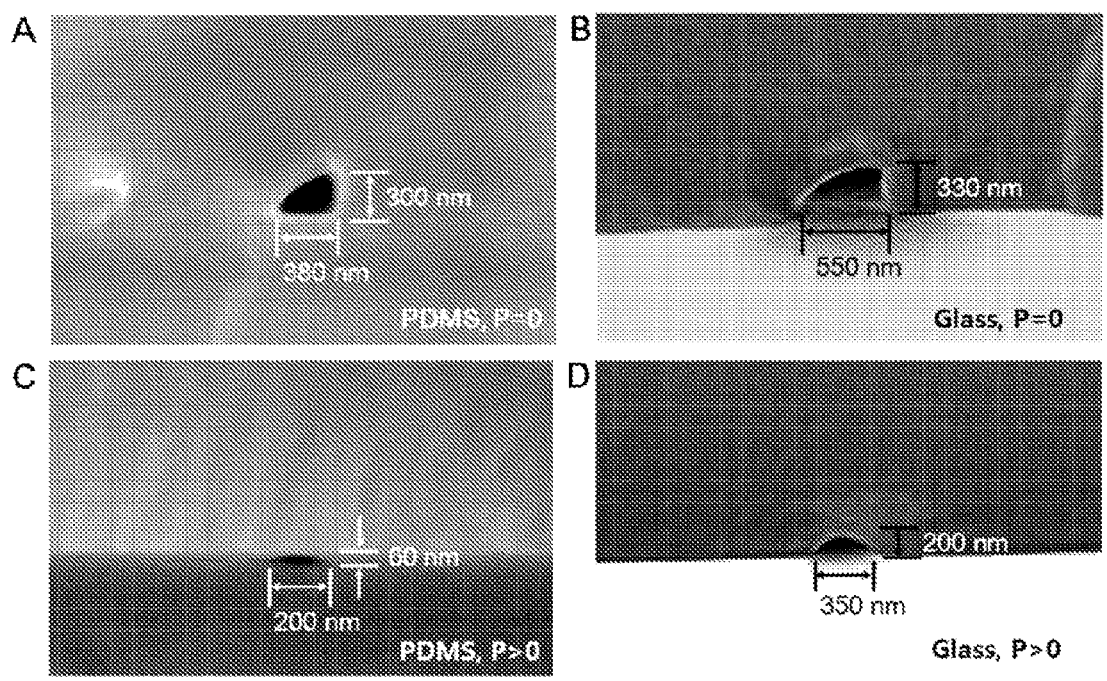
FIGS. 2A-D

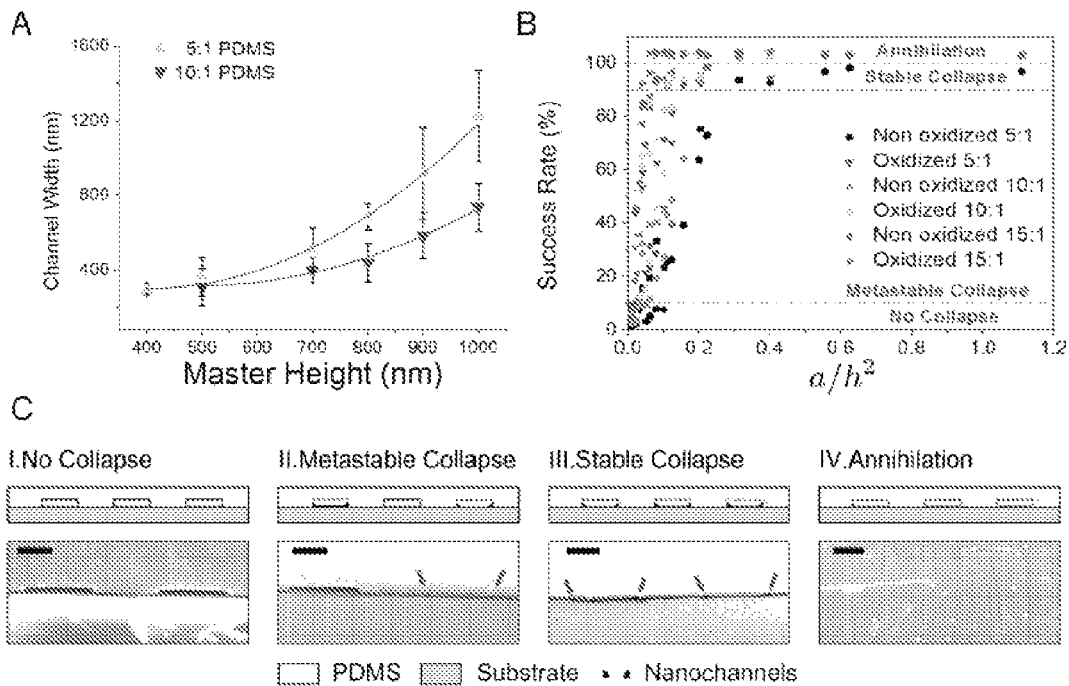
FIGS. 3A-C
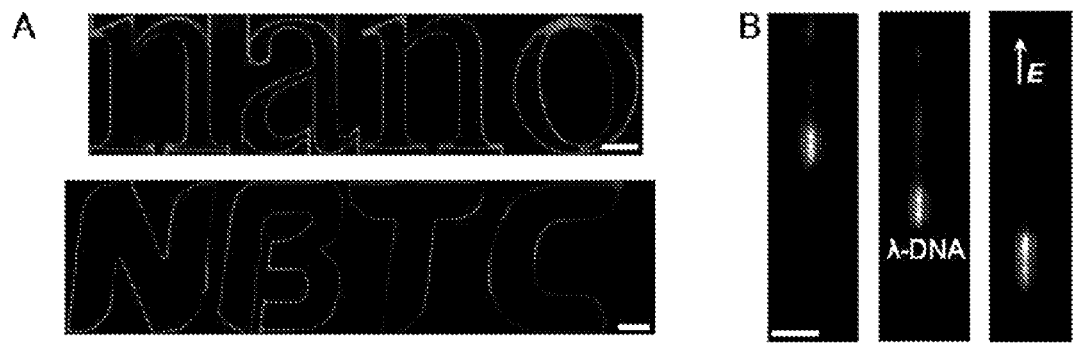
FIGS. 4A-B

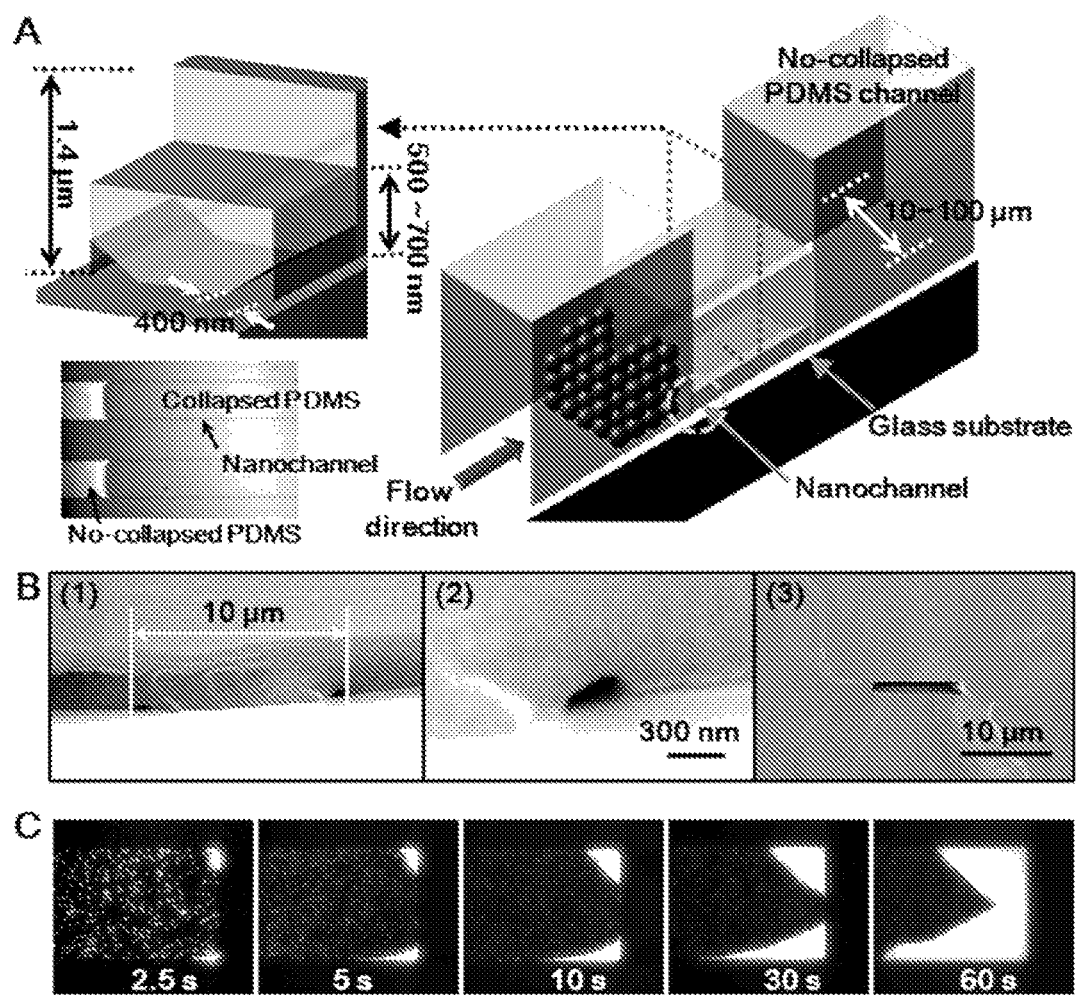
FIGS. 5A-C

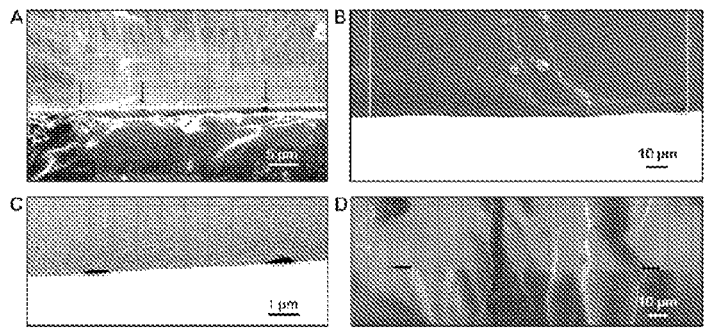
FIGS. 7A-D
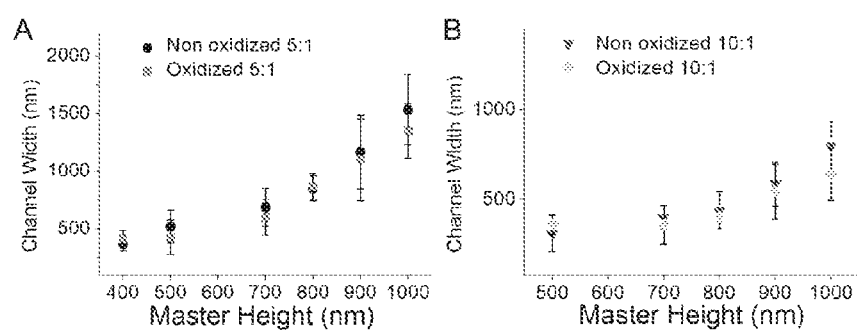
FIGS. 8A-B
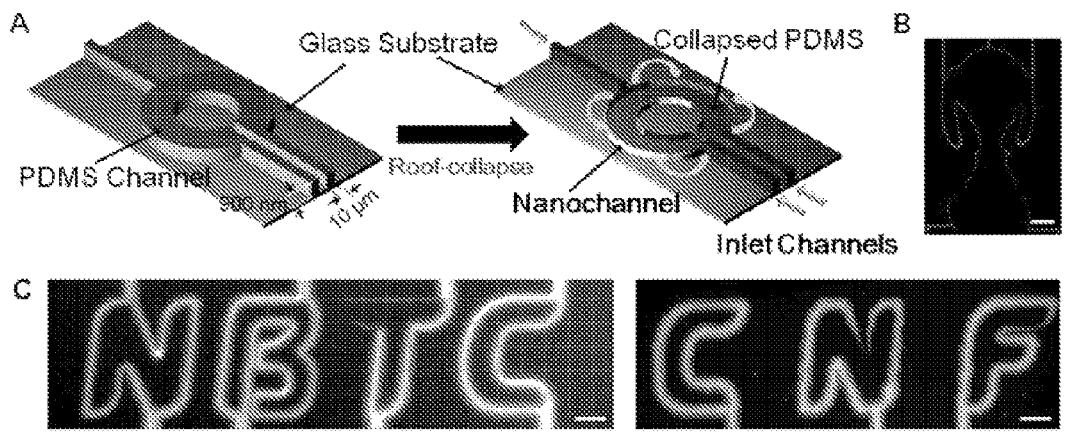
FIGS. 9A-C

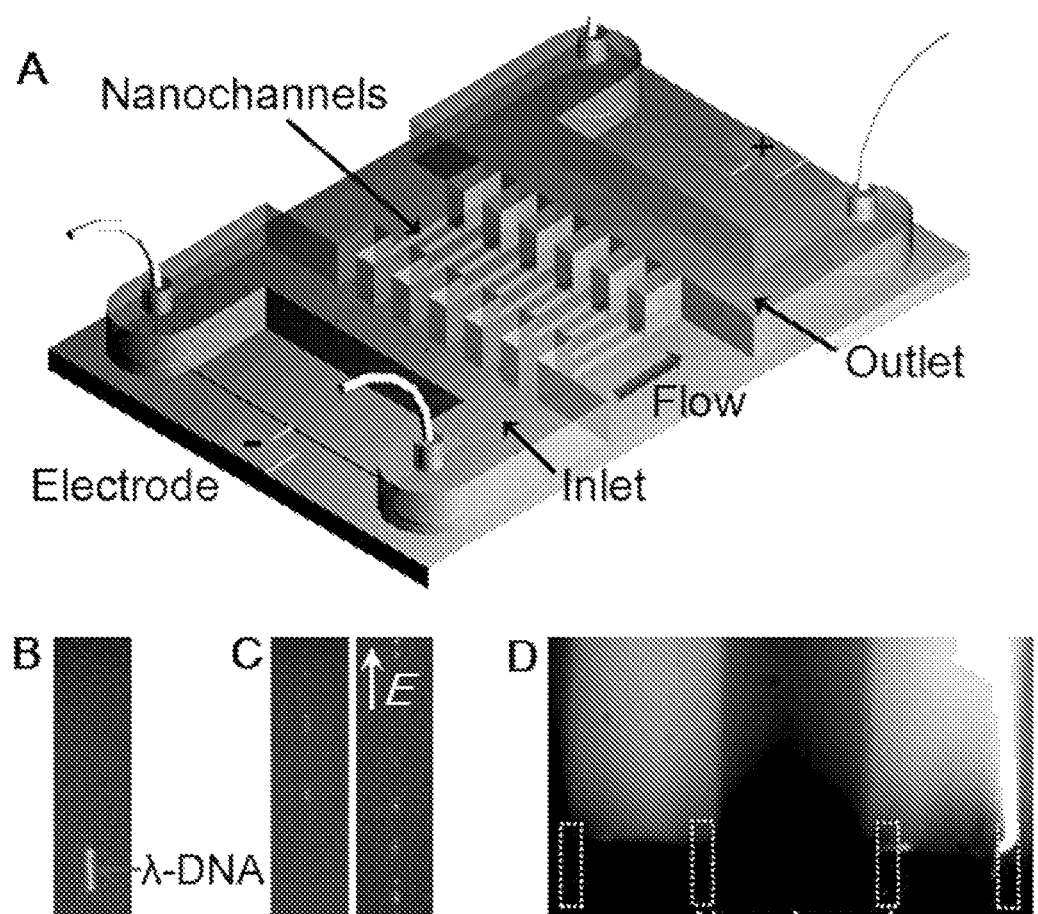
FIGS. 10A-D

NANOFILTER DEVICES USING ELASTOMERIC MICRO TO NANOCHANNEL INTERFACES AND METHODS BASED THEREON

CROSS-REFERENCE TO RELATED APPLICATIONS

This application claims priority to and the benefit of U.S. provisional patent application Ser. No. 61/236,074, entitled Fabrication of Nanofilter Devices Using Elastomeric Micro to Nanochannel Interfaces, filed Aug. 21, 2009, which is incorporated herein by reference in its entirety.

STATEMENT REGARDING FEDERALLY SPONSORED RESEARCH OR DEVELOPMENT

The disclosed invention was made with government support under grant no. R21EB007031 from the National Institutes of Health—National Institute of Biomedical Imaging and Bioengineering, agreement no. ECS-9876771 from the National Science Foundation, and grant no. ECS-9731293 from the National Science Foundation. The government has rights in this invention.

1. TECHNICAL FIELD

The present invention relates to nanofluidic systems and methods for fabricating them. The invention also relates to methods for fabricating nanochannels of desired dimensions in nanofluidic or microfluidic devices. The invention also relates to methods for manipulating single molecules in microfluidic devices. The invention also relates to methods for concentrating and detecting nanoscale particles.

2. BACKGROUND OF THE INVENTION

Nanofluidic applications, integrated with microfluidics have immense opportunities for tuning optical properties and manipulating small molecules such as proteins and DNA. Various techniques have been developed to fabricate nanometer-scale channels. Previously, electron beam lithography, focused ion beam milling techniques, interference lithography, and nano imprint lithography have been developed to pattern nano-scale trenches for this purpose. Alternate non-lithographic approaches have also been introduced to produce nanochannels (D. Huh, K L. Mills, X. Zhu, M. A. Burns, M. D. Thouless, S. Takayama, Nature Materials, 6, 624 (2007); S. Chung, J H. Lee, M-W. Moon, J. Han, R. D. Kamm, Advanced Materials, 20, 3011 (2008)).

Recently a number of nanofluidic fabrication techniques have been introduced that exploit the deformability of elastomeric materials like polydimethylsiloxane (PDMS). These techniques are limited in the complexity of the devices which can be fabricated, being able to only create straight or irregular channels normal to the direction of an applied strain.

Of the many reasons why nanofluidic systems are of interest, the most well developed applications revolve around sensing, detection, and species handling in single or "few" molecule environments (Hong J W, Quake S R (2003) Integrated nanoliter systems. Nature Biotechnol 21: 1179-1183; Tegenfeldt J O, et al. (2004) The Dynamics of Genomic-Length DNA Molecules in 100-nm Channels. Proc Natl Acad Sci USA 101: 10979-10983; Han J, Craighead H G (2000) Separation of Long DNA Molecules in a Microfabricated Entropic Trap Array. Science 288: 1026-1029; Fu J, Schoch R B, Stevens A L, Tannenbaum S R, Han J (2007) A patterned anisotropic nanofluidic sieving structure for continuous-flow separation of DNA and proteins. Nature Nanotech 2: 121-128; Austin R (2007) Nanofluidics: A fork in the nano-road. Nature Nanotech 2: 79-80; Riehn R, et al. (2005) Restriction mapping in nanofluidic devices. Proc Natl Acad Sci USA 102: 10012-10016; Daiguji H, Yang P, Szeri A J, Majumdar A (2004) Electrochemomechanical Energy Conversion in Nanofluidic Channels. Nano Lett 4: 2315-23211 Cowan M L, et al. (2005) Ultrafast memory loss and energy redistribution in the hydrogen bond network of liquid H2O. Nature 434: 199-202).

Researchers have recently demonstrated unique bioanalytical capabilities in nanofluidic devices including the ability to elongate single DNA molecules (Tegenfeldt J O, et al. (2004) The Dynamics of Genomic-Length DNA Molecules in 100-nm Channels. Proc Natl Acad Sci USA 101: 10979-10983), concentrate protein samples by more than four orders of magnitude (Lee J H, Chung S, Kim S J, Han J (2007) Poly(dimethylsiloxane)-Based Protein Preconcentration Using a Nanogap Generated by Junction Gap Breakdown. Anal Chem 79: 6868-6873) and to efficiently separate both large (Han J, Craighead H G (2000) Separation of Long DNA Molecules in a Microfabricated Entropic Trap Array. Science 288: 1026-1029; Chou H-P, Spence C, Scherer A, Quake S (1999) A microfabricated device for sizing and sorting DNA molecules. Proc Natl Acad Sci USA 96: 11-13) and small (Fu J, Schoch R B, Stevens A L, Tannenbaum S R, Han J (2007) A patterned anisotropic nanofluidic sieving structure for continuous-flow separation of DNA and proteins. Nature Nanotech 2: 121-128) biomolecules.

As a result of their technological promise, numerous methods have been developed to fabricate these systems including: electron beam lithography (Reccius C H, Stavis S M, Mannion J T, Walker L P, Craighead H G (2008) Conformation, Length, and Speed Measurements of Electrodynamically Stretched DNA in Nanochannels. Biophys J 95: 273-286; Mannion J T, Reccius C H, Cross J D, Craighead H G (2006) Conformational Analysis of Single DNA Molecules Undergoing Entropically Induced Motion in Nanochannels. Biophys J 90: 4538-4545), focused ion beam milling (Cao H, et al. (2002) Fabrication of 10 nm enclosed nanofluidic channels. Appl Phys Lett 81: 174-176), interference lithography (O'Brien II M J, et al. (2003) Fabrication of an integrated nanofluidic chip using interferometric lithography. J Vac Sci Technol B 21: 2941-2945), AFM lithography (Pellegrino L, et al. (2006) (Fe,Mn) 3O4 Nanochannels Fabricated by AFM Local-Oxidation Nanolithography using Mo/Poly(methyl methacrylate) Nanomasks. Adv Mater 18: 3099-3104) and nano-imprint lithography (Tegenfeldt J O, et al. (2004) The Dynamics of Genomic-Length DNA Molecules in 100-nm Channels. Proc Natl Acad Sci USA 101: 10979-10983; Xia Q, Morton K J, Austin R H, Chou S Y (2008) Sub-10 nm Self-Enclosed Self-Limited Nanofluidic Channel Arrays. Nano Lett 8: 3830-3833). The significant advantages of these high-end nanofabrication technologies are their high resolution, reproducibility and flexibility.

In spite of these advantages, these methods are somewhat limited to provide rapid prototyping of the nanofluidic systems. To augment these high-resolution techniques, several groups have developed nanofluidic fabrication in PDMS using lower resolution lithography methods. Huh et al. (Huh D, et al. (2007) Tuneable elastomeric nanochannels for nanofluidic manipulation. Nature Mater 6: 424-428) for example used crack formation in a surface oxide layer to make nanochannels with mechanically tunable widths. Similarly Chung et al. (Chung S, Lee J H, Moon M-W, Han J, Kamm R D (2008) Non-Lithographic Wrinkle Nanochannels for Protein Preconcentration. Adv Mater 20: 3011-3016) utilized wrinkles on an elastomeric PDMS surface which when bonded to another surface formed discrete nanochannels. While these approaches greatly simplify the fabrication of nanochannels, the complexity of the devices which can be created is relatively low, in that only straight lines orthogonal to the stretching force can be fabricated.

An additional challenge of nanofluidic fabrication with soft materials like PDMS is the relatively low stiffness of the material resulting in dimensional instability and even channel collapse to the point of sealing (Chou S Y, Krauss P R, Renstrom P J (1996) Imprint Lithography with 25-Nanometer Resolution. Science 272: 85-87). With the goal of determining the design rules which minimize these effects, Huang et al. (Huang Y Y, et al. (2005) Stamp Collapse in Soft Lithography. Langmuir 21: 8058-8068.; Zhou W, et al. (2005) Mechanism for stamp collapse in soft lithography. Appl Phys Lett 87: 251925-3) recently reported on the mechanism of channel collapse (also referred to as "roof" or "stamp" collapse) in soft lithography. Their work characterized many of the conditions under which the middle of a suspended channel structure will sag to the point of touching the lower (channel) substrate and permanently seal. Ultimately, the use of PDMS with higher stiffness or channels designs with a close to square cross section have been found to be good techniques to minimize these problems (Huh D, et al. (2007) Tuneable elastomeric nanochannels for nanofluidic manipulation. Nature Mater 6: 424-428; Thangawng A L, Swartz M A, Glucksberg M R, Ruoff R S (2007) Bond-Detach Lithography: A Method for Micro/Nanolithography by Precision PDMS Patterning. Small 3: 132-138; Kang H, Lee J, Park J, Lee H H (2006) An improved method of preparing composite poly(dimethylsiloxane) moulds. Nanotechnology 17: 197-200).

There is therefore a need in the art for methods for fabricating nanofluidic devices that use deformable elastomeric materials and that create complex nanochannel structures.

Citation or identification of any reference in Section 2, or in any other section of this application, shall not be considered an admission that such reference is available as prior art to the present invention.

3. SUMMARY OF THE INVENTION

The invention provides a method for fabricating a nanochannel comprising:
(a) providing a microchannel comprising a roof, a wall, and a bottom, the microchannel having a feature that promotes a desired frequency of microchannel collapse; and
(b) controlling collapse of the microchannel to create a nanochannel defined or enclosed by a portion of the collapsed roof, the wall, and a portion of the bottom of the microchannel.

In one embodiment, the step of controlling collapse of the microchannel comprises controlling collapse of the roof of the microchannel.

In another embodiment, the microchannel comprises a collapsible material.

In another embodiment, the roof of the microchannel comprises the collapsible material.

In another embodiment, the collapsible material is an elastomer.

In another embodiment, the elastomer is polydimethylsiloxane (PDMS).

In another embodiment, the height of the nanochannel is less than or equal to 100 nm.

In another embodiment, the height of the nanochannel is 60-100 nm

In another embodiment, the step of controlling collapse of the microchannel comprises the step of determining conditions under which the microchannel will collapse and the nanochannel will form.

In another embodiment, the step of determining desired parameters of the microchannel that can be varied to obtain a desired nanochannel height and width.

In another embodiment, the $a/h^2$ value of the microchannel is in a range in which roof collapse is likely.

In another embodiment, the step of controlling collapse of the microchannel comprises the step of applying a compressive force to the microchannel.

In another embodiment, the step of providing the microchannel comprises the steps of:
providing a molded or patterned collapsible material, the molded or patterned collapsible material having a geometric feature, a stiffness feature or a flexibility feature that promotes a desired frequency of microchannel collapse;
providing a base; and
bonding the molded or patterned collapsible material to the base, thereby forming the microchannel.

In one embodiment, the base is elastomer, polymer, glass or silicon.

In another embodiment, the molded or patterned collapsible material is an elastomer.

In another embodiment, the step of providing the molded or patterned collapsible material comprises the step of nano imprinting or micro imprinting collapsible material or precursor collapsible material to form the molded or patterned collapsible material.

In another embodiment, the step of providing the molded or patterned collapsible material comprises the steps of:
providing a master, wherein the master is configured to have a geometric condition that promotes a desired frequency of microchannel collapse;
forming the molded or patterned collapsible material on the master, the molded or patterned collapsible material having a material stiffness that promotes a desired frequency of microchannel collapse; and
removing the molded or patterned collapsible material from the master.

In another embodiment, the step of forming the molded or patterned collapsible material on the master comprises the step of casting or molding precursor collapsible material on the master.

In another embodiment, the method comprises, after the step of casting or molding precursor collapsible material on the master, the step of curing the precursor collapsible material to form the molded or patterned collapsible material.

In another embodiment, the master is a sacrificial material.

In another embodiment, the master comprises a photoresist or a deposited layer of metal (e.g., aluminum).

In another embodiment, the master comprises two or more interfaced masters of mismatched width.

In another embodiment, the step of providing a master comprises the step of making the master from a pattern, wherein the pattern is configured to have a geometric condition that promotes a desired frequency of microchannel collapse and wherein the pattern has a desired nanochannel and/or microchannel layout.

In another embodiment, the pattern is on a silicon wafer.

A method is also provided for fabricating a microchannel to nanochannel transition (or interface) comprising:

(a) providing a first microchannel and a second microchannel, wherein at least the first microchannel comprises a roof, a wall, and a bottom, and has a feature that promotes a desired frequency of microchannel collapse; and (b) controlling collapse of the first and second microchannels whereby the first microchannel collapses to create a nanochannel defined or enclosed by a portion of the collapsed roof, the wall, and a portion of the bottom of the first microchannel, and the second microchannel does not collapse or collapses to form a smaller microchannel, whereby the nanochannel and the microchannel are operatively connected after the collapse.

In another embodiment, the first and second microchannels are connected prior to the collapse.

In another embodiment, the first microchannel or the second microchannel are connected to a plurality of microchannels.

A method is also provided for fabricating a nanofluidic or microfluidic device comprising the step of fabricating a nanochannel, wherein the step of fabricating the nanochannel comprises:

(a) providing a microchannel comprising a roof, a wall, and a bottom, the microchannel having a feature that promotes a desired frequency of microchannel collapse; and (b) controlling collapse of the microchannel to create a nanochannel defined or enclosed by a portion of the collapsed roof, the wall, and a portion of the bottom of the microchannel.

In one embodiment, the $a/h^2$ value of the microchannel is in a range in which roof collapse is likely and wherein a nanochannel is produced.

In another embodiment, the method further comprises the step of fabricating a microchannel on the device, wherein the step of fabricating the microchannel comprises:

providing a second microchannel; and controlling collapse of the second microchannel wherein the microchannel does not collapse or collapses to form a smaller microchannel.

In another embodiment, the $a/h^2$ value is in a range in which roof collapse is unlikely and wherein a microchannel is produced.

A nanofluidic or microfluidic device is also provided comprising a nanochannel wherein the height of the nanochannel is less than or equal to 100 nm.

In one embodiment, the height of the nanochannel is 60-100 nm.

A nanofluidic or microfluidic device is also provided comprising a microchannel to nanochannel transition (or interface).

In one embodiment, the height of the nanochannel is less than or equal to 100 nm.

In another embodiment, the height of the nanochannel is 60-100 nm.

In another embodiment, the device can be a sample concentration device.

A nanofluidic or microfluidic device comprising a nanochannel, wherein the nanochannel is produced by the method for fabricating a nanochannel disclosed herein.

In one embodiment, the device also comprises a microchannel, wherein the microchannel is produced by the methods for fabricating a nanochannel disclosed herein.

In one embodiment, the microchannel and the nanochannel are fluidically connected at an interface.

In another embodiment, the microchannel and the nanochannel are fluidically connected at an interface.

A method for detecting an analyte of interest is also provided comprising the steps of:

providing a nanochannel, wherein the nanochannel has a height ≤100 nm;

introducing a fluidic sample suspected of containing the analyte of interest into the nanochannel;

flowing the fluidic sample in the nanochannel; and detecting the presence or absence of the analyte in the nanochannel.

In one embodiment, the step of providing a nanochannel comprises the step of providing a nanofluidic or microfluidic device comprising the nanochannel.

In another embodiment, the analyte is a nucleic acid, the flowing step comprises the step of electrophoretically driving the nucleic acid in the nanochannel, thereby stretching the nucleic acid, and the detecting step comprises detecting the stretched nucleic acid.

In another embodiment, the detecting step comprises performing optical imaging.

In another embodiment, the detecting step comprises performing surface enhanced Raman scattering (SERS).

In another embodiment, the nanochannel has a height of 60-100 nm.

In another embodiment, the nanofluidic or microfluidic device additionally comprises a microchannel, and the nanochannel is fluidically connected to the microchannel by a microchannel to nanochannel transition.

In another embodiment, the step of flowing the fluidic sample in the nanochannel thereby concentrates the analyte at the microchannel to nanochannel transition.

A method for prototyping a nanofluidic or microfluidic device is also provided comprising the step of fabricating a nanochannel using the methods disclosed herein.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1A. Schematic illustrating the method for fabricating a nanochannel comprising the "roof-collapse" technique. (A) Two dimensional representation of the fabrication process. For clarity, the thicknesses of the various layers on the substrate are not drawn to scale. Upper diagram: A thin layer of photoresist or evaporated metal is deposited on the substrate and lithographically patterned to the desired channel layout. Since the channel size is dependent on the height of the master the resolution with which the channels can be patterned is not important. Patterning different thicknesses allows interfacing of different channel size. Middle diagram: After patterning, the PDMS solution is cast onto the master. Lower diagram: The molded PDMS elastomer (also referred to herein as a "PDMS mold") is then removed and bonded to a base (also referred to herein as a "plain substrate") such as glass, silicon or elastomer.

FIG. 1B. Three dimensional representation of the fabrication process. Various pattern shapes can be used as a nanochannel template. "Roof collapse" of the PDMS leaves behind a nanochannel at the edge. The inset indicates that triangular shaped nanochannels were formed after the roof collapse.

FIGS. 2A-D. SEM images of nanochannels. (A) Bonding of molded PDMS elastomer to a PDMS plain substrate (base) results in nanochannels with a triangular cross-section. (B) Molded PDMS elastomer-cover glass plain substrate bonding results in larger channel width owing to its elastic moduli mismatch. (C) With a controlled 50 kPa normal stress is applied, to a molded PDMS elastomer-PDMS plain substrate system much smaller channels result. The same molded PDMS elastomer as in (A) was used to form the smaller channel shown here. (D) Compressed nanochannel in molded PDMS elastomer-cover glass plain substrate. Again the same molded PDMS elastomer as (B) was used.

FIGS. 3A-C. Nanochannel characterizations. (A) Channel width is plotted against master's height for both 10:1 PDMS and 5:1 PDMS. Owing to their different elastic moduli, generally 10:1 PDMS nanochannel yields smaller widths than that of 5:1. (B) The nanochannel formation rate is characterized as a function of $a/h^2$, for different elastic moduli (5:1, 10:1, and 15:1) and oxidized vs. non-oxidized PDMS. Each dash line represents the "No collapse", "Metastable collapse", "Stable collapse", and "Annihilation" regions. (C) Schematic representations of four regions in (B). Each region is accompanied with its SEM counterpart. The red arrows indicate the location of the nanochannels (scale bars: 10 μm).

FIGS. 4A-B. Optical images of complex nanochannels (A) and manipulation of a single DNA molecule along a straight nanochannel (B). (A) Nanofluidic representations of "nano" and "NBTC" (the abbreviation for the Nanobiotechnology Center at Cornell University). Complex nanofluidic networks are possible with this technique. All these nanochannels are formed with at least one axis in nanometer regime. (scale bar: 100 μm and 50 μm, respectively). For a demonstration purpose, each letter is taken individually and then combined together. (B) Electrophoretic migration of the λ-DNA in a straight nanochannel by 40 V cm$^{-1}$ (0.5 sec interval between the images.) Electric field is represented by E (scale bar: 5 μm).

FIGS. 5A-C. Interfacing nanofluidics with microfluidics and demonstration of a nanofluidic concentration ("nanofilter") device. (A) The nanofluidic concentration device shown in this embodiment comprises a plurality of functionally interfaced channels: A micrometer scale channel fabricated from a double thickness master and two nanoscale channels fabricated from the collapse of a single layer thickness master. Schematic representation of the operation of the device shows the concentration of nanoparticles at the interface between the microchannel and the nanochannel (B) SEM images of (1-2) the nanofluidic channel (400 nm width×300 nm height) and (3) microfluidic channel (10 μm width×1.4 μm height). (C) Time-lapse images of concentration of 700 nm polystyrene nanoparticles at the interface between microchannel and nanochannel.

Figure 6:
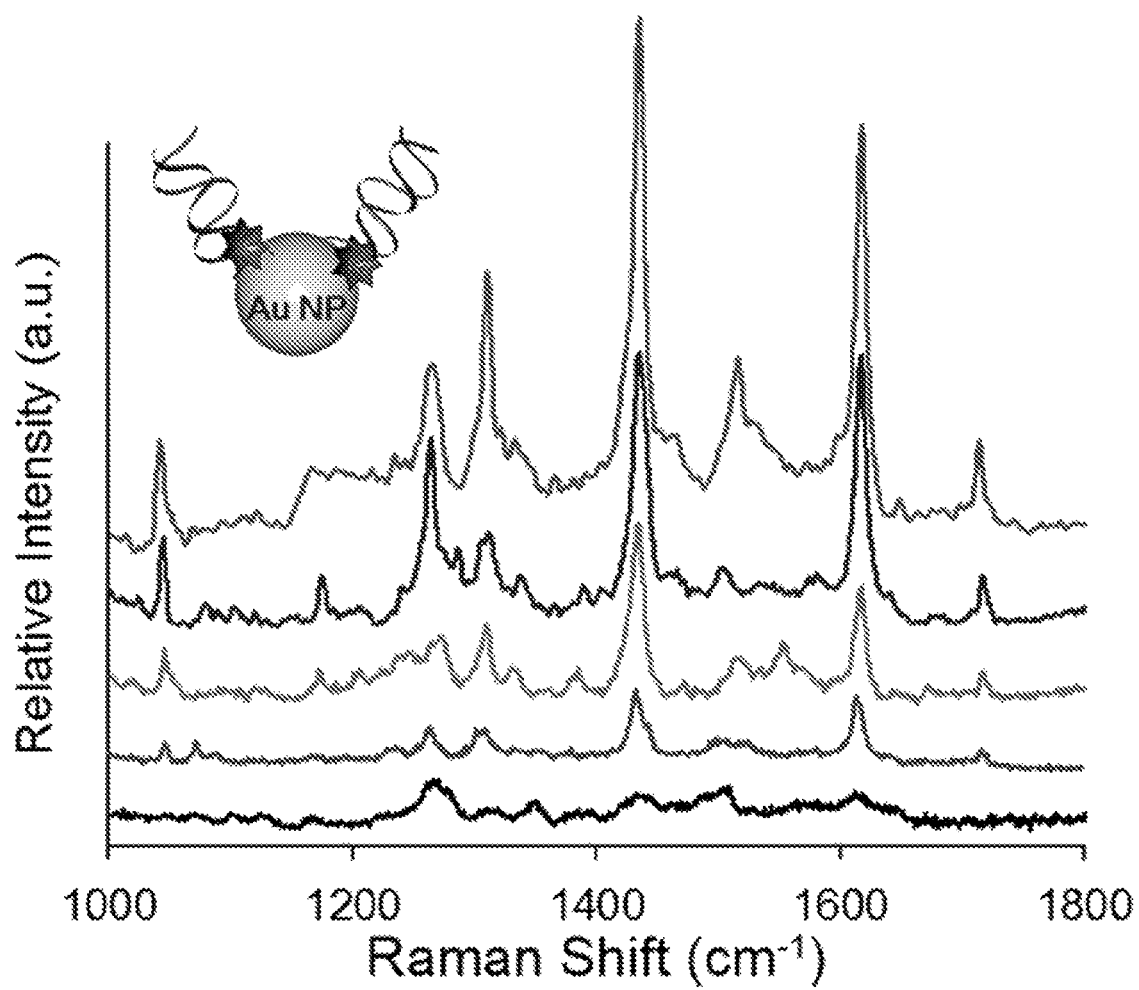

FIG. 6. SERS spectra of 3 nM Cy3-labelled DENV-4a. After introducing the 60 nm Au colloid solution by applying electric field of 40 V cm$^{-1}$ the SERS emission at the interface between nanochannels and microchannel was monitored as a function of time. (1) 5 s, (2) 10 s, (3) 20 s, (4) 40 s, and (5) 60 s. As expected, the intensity of the signal increases with the accumulation and aggregation of SERS emitters.

FIGS. 7A-D. Various SEM images of nanochannels with different configurations. (A) Nanochannels with 10 μm and 20 μm apart from each other at the PDMS-PDMS interface. (B) 100 μm apart nanochannels formed at a PDMS-cover glass interface. (C) 10 μm apart nanochannels formed by roof collapse at a PDMS-cover glass interface. The lateral and vertical dimensions of the nanochannels shown here are smaller than 1 μm. (D) Microchannels with 10 μm by 1.4 μm dimensions, which are resistant to roof collapse.

FIGS. 8A-B. Plot of channel width against master height for both 10:1 PDMS and 5:1 PDMS. (A) Relationship between the PDMS master height and nanochannel width for 5:1 elastomer/base mixture. There is no significant channel width difference in the oxidized PDMS and non-oxidized PDMS. (B) Relationship between the PDMS master height and nanochannel width for 10:1 elastomer/base mixture. Again, no significant difference in nanochannel width was found in comparing both non-oxidized and oxidized PDMS.

FIGS. 9A-C. Optical images showing various PDMS micro-/nanochannel designs. (A) Schematic illustration of the "O" letter formation using this method. Because the nanochannel layout matches that of its master the nanochannels can be formed into very complex patterns without much restraint (so long as the master holds a looped curve). (B) Micro and nanofluidic representations of Snoopy (cartoon character) image (scale bar: 50 μm). (C) CNF and NBTC Logo without oxidization process (scale bars: 50 μm). Apart from FIG. 4SB and C, these fluidic systems did not undergo an oxidization exposure step.

FIGS. 10A-D. Micro-/nanofluidic device for DNA elongation and nanoparticle concentration. (A) Schematic representation of nanofluidic device. (B) Fluorescent image of the stationary λ-DNA elongated along the nanochannel (no external electric field applied, scale bar: 5 μm). (C) Fluorescent images of λ-DNAs elongated along the nanochannels. Two different lengths of elongated DNA are shown for the different nanochannel sizes (Scale bar: 2 μm). (D) Concentration of 45 nm polystyrene nanoparticles at the interface between microchannel and nanochannel The same micro/nano fluidic interface as used in FIG. 5C is shown. The "Bottle Neck" effect of the micro/nano interfaces amasses the nanoparticles in spite of their smaller size than that of nanochannels. The operating electric field is 40 V cm$^{-1}$.

5. DETAILED DESCRIPTION OF THE INVENTION

For clarity of disclosure, and not by way of limitation, the detailed description of the invention is divided into the subsections set forth below.

5.1 Method for Fabricating a Nanochannel

A method is provided for fabricating a nanochannel. The method comprises the step of controlling collapse of a microchannel structure.

A nanochannel can be any channel ranging in size from 1 nm to 1000 nm (1 μm) that is positioned in or on a nanofluidic or microfluidic device referred collectively herein as "microfluidic device(s)") A microchannel can be any channel ranging in size from 1 μm (1000 nm) to 1000 μm (1 mm) that is positioned in or on the microfluidic device. In other embodiments, a microchannel can be a channel that is larger than 1 mm that is positioned in or on the microfluidic device.

In one embodiment, the method for fabricating a nanochannel can comprise:

(a) providing a microchannel comprising a roof, a wall, and a bottom, the microchannel having a feature that promotes a desired frequency of microchannel collapse; and (b) controlling collapse of the microchannel to create a nanochannel defined or enclosed by a portion of the collapsed roof, the wall, and a portion of the bottom of the microchannel.

In another embodiment, the step of providing the microchannel comprises the steps of:

providing a molded or patterned collapsible material, the molded or patterned collapsible material having a geometric feature, a stiffness feature or a flexibility feature that promotes a desired frequency of microchannel collapse;

providing a base; and bonding the molded or patterned collapsible material to the base, thereby forming the microchannel.

In another embodiment, the step of providing the molded or patterned collapsible material comprises the steps of:

providing a master, wherein the master is configured to have a geometric condition that promotes a desired frequency of microchannel collapse;

forming the molded or patterned collapsible material on the master, the molded or patterned collapsible material having a material stiffness that promotes a desired frequency of microchannel collapse; and removing the molded or patterned collapsible material from the master.

The method employs the art-known properties of a collapsible material, e.g., an elastomer, to form a nanochannel or microchannel. The location of a desired channel can be determined by the location of a transition between the thin and thick sections of features that have been patterned or molded in collapsible material. The method combines the dimensional range and network complexity that can be obtained from high end nanofabrication techniques with the simplicity of recently demonstrated non-lithography approaches.

In one embodiment, the method can comprise providing a microchannel of the collapsible material. The method can further comprise controlling collapse of the microchannel so that the microchannel collapses to form a nanochannel of desired dimensions in the elastomer. According to the method, the channel size can be defined by the height of the transition between thick and thin molded collapsible material, or by the edge of the void created when a molded layer of collapsible material is flipped and applied on a planar substrate. According to the method, the width of the feature molded in the collapsible material does not define the finished size of the nanochannel or microchannel, provided it is over a certain width as described hereinbelow.

Collapsible or deformable material can be selected that has a material stiffness (which stiffness is either known in the art or determined by art known methods) that also promotes a desired frequency of microchannel collapse.

In certain embodiments, a precursor or solution of the collapsible material, e.g., an elastomer solution, is cast onto a master (or template) that is patterned with a desired feature for the microchannel. The precursor collapsible material is cured to create molded or patterned collapsible material. The molded or patterned collapsible material is removed from the master and bonded to a base, thereby forming the microchannel. The microchannel then collapses (or is collapsed) to form a nanochannel of desired dimensions.

The properties of the collapsible material can be used to control the dimensions of a nanochannel formed in the nanofluidic or microfluidic device with great accuracy. Any collapsible or deformable material known in the art to be flexible enough to collapse under some set of known or predicted conditions (e.g., elastomer, polymer, etc.) can be used according to the methods of the invention. In one embodiment, the method employs the properties of a collapsible material, e.g., an elastomer such as polydimethyisiloxane (PDMS), to form a nanochannel. In another embodiment, the collapsible material is glass, and the collapse is performed under conditions near the glass transition temperature. Other collapsible plastic materials, e.g., cyclic olefin polymer (COP) are also known in the art (S. Park, K. H. Lee, H. G. Craighead, On-chip Coupling of Electrochemical Pumps and an SU-8 tip for Electrospray Ionization Mass Spectrometry, Biomedical Microdevices 10 (6), 891-897 (2008) doi:10.1007/s10544-008-9203-6; Y. Yang, C. Li, J. Kameoka, K. H. Lee, H. G. Craighead, A Polymeric Microchip with Integrated Tips and In Situ Polymerized Monolith for Electrospray Mass Spectrometry, Lab on a Chip 5, 869-876 (2005). DOI: 10.1039/b503025k; Y. Yang, C. Li, K. H. Lee, H. G. Craighead, Coupling On-Chip Solid-Phase Extraction to Electrospray Mass Spectrometry Through an Integrated Electrospray Tip, Electrophoresis 26 (19), 3622-3630 (2005)). Such collapsible or flexible materials can be used for fabricating nanochannels.

Cyclic olefin polymer (COP), for example, has a glass transition temperature around 107° C. Thus two plates of COP can be easily bonded by using a hot press and methods known in the art. Because of this glass transition temperature, one side can be embossed, e.g., with the wall(s) and roof (or top or ceiling) of a microchannel, and bonded to the other side (the base), which will form the bottom or floor of the microchannel. While bonding the two plates together, applying controlled pressure would cause collapse of the embossed microchannel structure to form one or more nanochannels.

The methods provided herein enable nanochannels of predictable dimensions to be formed. The methods are also compatible with the integration of electronic components on the nanofluidic or microfluidic device.

The method for fabricating a nanochannel uses the easily controlled vertical dimension of a feature molded in a collapsible, flexible or deformable material to precisely define the desired finished size of a nanochannel or microchannel. Once the collapsible or deformable (e.g., elastomer) layer of material is positioned on a base, the thin section of the collapsible material will collapse into the void, bonding where it meets the base. Where the thin and thick layers of the collapsible material meet, however, the properties of the collapsible material will limit the amount of bending of the thin section of the collapsible material and will prevent the thin section from collapsing all the way to the bottom of the void/channel. The thin section cannot bend or collapse a full 90 degrees. If it did so, it would touch the wall of the void formed by the thick section, and would fill the juncture formed by the meeting of the base and the thick section of the collapsible material forming the two side walls. By preventing this complete disappearance of the void/channel, this property of the collapse consequently defines a channel which, because of the partial collapse of the original channel, is much smaller than the original channel. The thickness of the thin layer, the difference in thickness between the thin and thick layers, the properties of the collapsible material, and conditions under which collapse will occur (e.g., temperature) will determine the size and shape of the nanochannel formed by the collapse of the thin layer. Thus for a given material under given conditions, a nanochannel of desired size can be created simply by appropriately sizing the thickness of the thin and thick layers of the collapsible material.

According to the method, to achieve nanometer scale control over channel dimensions, only a process that can define the Z dimension of the collapsible material to the nanometer scale is needed. It is not necessary to similarly finely control the X or Y dimensions. As a result, lithography methods with only micrometer-scale (microscale) control over the X and Y dimensions, but with nanometer-scale (nanoscale) control over the Z dimension, can now be used to create nanometer-scale channels.

By using channel (roof) collapse, the easy-to-control vertical dimension of a collapsible material (e.g., elastomer) can be converted to the lateral dimension of a nanochannel. Complex nanochannel structures can be fabricated wherein the height of the nanochannel is 1-10 nm, 10-20 nm, 20-30 nm, 30-40 nm, 40-50 nm, 50-60 nm, 60-70 nm, 70-80 nm, 80-90 nm, 90-100 nm, 100-500 nm or 500 nm-1000 nm (1 μm). In one embodiment, the nanochannel height is as low as 60 nm In another embodiment, the nanochannel height is 60-100 nm.

The method for fabricating a nanochannel can comprise the step of determining the conditions under which a microchannel structure will collapse and a nanochannel will form. Determination of such conditions is known in the art. Under controllable conditions, a system can be fabricated to collapse in such a way so as to leave nanofluidic channels as low as 60 nm that are produced from low resolution, but highly complex, photolithographic patterns.

In one embodiment, the method can comprise the steps of determining the material stiffness and/or the geometric conditions that lead to microchannel collapse and determining desired parameters that can be varied to obtain a desired nanochannel size. Such methods for determining material stiffness and/or geometric conditions are known in the art.

The method can be used to form a nanochannel in a nanofluidic or microfluidic device. A method is provided for fabricating a nanofluidic or microfluidic device comprising the step of fabricating a nanochannel, wherein the step of fabricating the nanochannel comprises:

(a) providing a microchannel comprising a roof, a wall, and a bottom, the microchannel having a feature that promotes a desired frequency of microchannel collapse; and (b) controlling collapse of the microchannel to create a nanochannel defined or enclosed by a portion of the collapsed roof, the wall, and a portion of the bottom of the microchannel.

In one embodiment, the $a/h^2$ value of the microchannel is in a range in which roof collapse is likely and where a nanochannel is produced. Structures can be designed and built on a nanofluidic or microfluidic device, with an $a/h^2$ value in the range in which roof collapse is likely (preferably highly likely) to happen and hence, nanochannel formation is likely (preferably highly likely), Determining an $a/h^2$ value in the range in which roof collapse is likely (or highly likely) is known in the art (e.g., Huang Y Y, et al. (2005) Stamp Collapse in Soft Lithography. Langmuir 21: 8058-8068; Zhou W, et al. (2005) Mechanism for stamp collapse in soft lithography. Appl Phys Lett 87: 251925-3).

In other embodiments, structures can be built on a nanofluidic or microfluidic device in which the $a/h^2$ value is in the range in which roof collapse is not likely to happen, thus producing a microchannel.

In another embodiment, the method further comprises the step of fabricating a microchannel on the device, wherein the step of fabricating the microchannel comprises:

providing a second microchannel; and
controlling collapse of the second microchannel wherein the microchannel does not collapse or collapses to form a smaller microchannel.

In another embodiment, the $a/h^2$ value is in a range in which roof collapse is unlikely and wherein a microchannel is produced.

A method is also provided for fabricating a microchannel to nanochannel transition comprising:

(a) providing a first microchannel and a second microchannel; and (b) controlling collapse of the first and second microchannels whereby the first microchannel collapses to form a nanochannel and the second microchannel does not collapse or collapses to form a smaller microchannel, whereby the nanochannel and the microchannel are operatively connected after the collapse.

In another embodiment, the first and second microchannels are connected prior to the collapse.

In another embodiment, the first microchannel or the second microchannel are connected to a plurality of microchannels.

The type of transition that results will be determined by the stiffness and geometric conditions established for the desired collapse. The collapsible material will bend at the edge of the void created by the transition from thick to thin, and the amount that it bends will be determined by its stiffness, geometry and other pre-determined conditions. When the bend is defined by more than one transition (i.e., a narrow one and a wide one), the material will find a solution to the bending problem naturally (spontaneously) such that it provides a smooth transition between two channels of different width.

A method is also provided for fabricating a nanofluidic or microfluidic device comprising the step of fabricating a nanochannel on the device, wherein the step of fabricating a nanochannel comprises providing a microchannel; and controlling collapse of the microchannel wherein the microchannel collapses to form a nanochannel. In one embodiment, the method can further comprise the step of fabricating a microchannel on the device, wherein the step of fabricating the microchannel comprises providing a second microchannel; and controlling collapse of the second microchannel wherein the microchannel does not collapse or collapses to form a smaller microchannel.

FIGS. 1A-B are schematic illustrations of one embodiment of the method for fabricating a nanochannel. Under the proper conditions, when placed in conformal contact, a microchannel collapses and the roof of the microchannel bonds to the lower substrate, forming a nanochannel. The nanochannel formation rate is characterized as a function of $a/h^2$, for different elastic moduli (5:1, 10:1, and 15:1) and oxidized vs. non-oxidized PDMS (FIG. 3B). As discussed above, determining an $a/h^2$ value in the range in which roof collapse is likely (or highly likely) is known in the art (e.g., Huang Y Y, et al. (2005) Stamp Collapse in Soft Lithography. Langmuir 21: 8058-8068; Zhou W, et al. (2005) Mechanism for stamp collapse in soft lithography. Appl Phys Lett 87: 251925-3).

FIG. 1A, a thin layer of photoresist or evaporated metal is deposited on a pattern substrate (e.g., a silicon wafer) and lithographically patterned to the desired channel layout. Since the channel size is dependent on the height of the master the resolution with which the channels can be patterned is not important. Patterning different thicknesses allows interfacing of different channel size. After patterning the master, an elastomer (e.g., PDMS) solution is cast onto the master. The molded elastomer (e.g., PDMS) is then removed and bonded to a plain (e.g., glass, silicon wafer or elastomer) substrate to form nanochannels and/or microchannels.

FIG. 1B shows three dimensional representation of this fabrication process. Various pattern shapes or materials can be used for a nanochannel master or template. In the embodiment illustrated in FIG. 1B, a pattern for a desired nanochannel and/or microchannel layout is made on a silicon wafer ($Si/SiO_2$). The master (template) is made of a photoresist (e.g., SU-8, as show in the diagram) or a deposited layer of metal (e.g., aluminum) that is deposited on the silicon wafer (upper left of FIG. 1B). An elastomer (e.g., PDMS) solution is cast onto the master (upper right of FIG. 1B). The molded elastomer is removed from the master and bonded to a substrate (e.g., glass or elastomer) (lower right of FIG. 1B).

"Roof collapse" of the PDMS leaves behind a nanochannel at the edge (lower left of FIG. 1B). The illustration at the lower left of FIG. 1B also illustrates 3 nanochannels formed in this particular embodiment. The inset in FIG. 1B indicates that triangular shaped nanochannels were formed after the roof collapse.

Using art known methods and knowledge about the mechanism of channel collapse (also referred to as "roof" or "stamp" collapse) in soft lithography (e.g., Huang Y Y, et al. (2005) Stamp Collapse in Soft Lithography. Langmuir 21: 8058-8068; Zhou W, et al. (2005) Mechanism for stamp collapse in soft lithography. Appl Phys Lett 87: 251925-3), the conditions under which the middle of a suspended channel structure will sag to the point of touching the lower substrate and permanently seal can be readily determined by the ordinarily-skilled artisan.

In another embodiment, art known methods of nano imprint (or micro imprint) lithography can be used to pattern the collapsible material.

In another embodiment, the collapsible material (or a precursor of the collapsible material, e.g., an elastomer solution) can be cast on a master (template) that is a sacrificial material. After curing, the master can be dissolved away, leaving the molded collapsible material.

To measure the dimensions of a fabricated nanochannel or microchannel, scanning electron microscopy (SEM) image analysis of the cross-section of a fractured channel can be performed using methods known in the art (FIGS. 2A-D). Most nanochannels fabricated using the method for fabricating a nanochannel, wherein channel collapse is induced without a compressive force being applied, will have a triangular cross-section (FIGS. 2A-B). When the microchannel is subject to a compressive force during channel collapse, the nanochannel formed will generally be semi-circular (FIGS. 2C-D).

5.2 Nanofluidic or Microfluidic Devices Comprising Nanochannels and Methods Based Thereon Nanofluidic devices and microfluidic devices are provided that comprise complex nanochannel structures produced by the methods of the invention. Micro- and nano-channels can be easily integrated into a single device. Methods are also provided for analyzing or detecting analytes of interest using nanofluidic and microfluidic devices comprising nanochannels produced by the methods disclosed herein.

Nanofluidic devices generally comprise channel structures that are at the nanoscale level ("nanochannels," e.g., 1 nm-1000 nm), but in certain embodiments may also comprise channels that are at the microscale level ("microchannels," e.g., 1 µm to 1000 µm or larger). Similarly, microfluidic devices generally comprise channel structures that are at the microscale level (e.g., 1 µm to 1000 µm or larger), but in certain embodiments may also comprise channels that are at the nanoscale level (e.g., 1 nm-1000 nm). As used hereinbelow, the term "microfluidic device" encompasses a fluidic device that comprises nanochannels, microchannels or both nanochannels and microchannels.

In one embodiment, a nanofluidic or microfluidic device is provided comprising a nanochannel wherein the height of the nanochannel is ≤100 nm. In another embodiment, the height of the nanochannel is 1-10 nm, 10-20 nm, 20-30 nm, 30-40 nm, 40-50 nm, 50-60 nm, 60-70 nm, 70-80 nm, 80-90 nm, 90-100 nm, 100-500 nm or 500 nm-1000 nm (1 µm). In one embodiment, the nanochannel height is as low as 60 nm. In another embodiment, the nanochannel height is 60-100 nm.

Nanofluidic or microfluidic devices can be produced by the methods of the invention that comprise microchannels in addition to nanochannels. In one embodiment, the nanofluidic or microfluidic device comprises a nanochannel of a desired dimension, wherein the nanochannel is produced by providing a microchannel; and controlling collapse of the microchannel as described in Section 5.1, whereby the microchannel collapses to form the nanochannel.

A nanofluidic or microfluidic device is also provided that comprises a microchannel to nanochannel transition (or interface) as described hereinabove.

In one embodiment, the nanofluidic or microfluidic device comprises a microchannel and a nanochannel, wherein the microchannel and the nanochannel are operatively (e.g., fluidically) connected at an interface as described herein. In another embodiment, the first and second microchannels are connected (i.e., prior to collapse).

In another embodiment, the first microchannel or the second microchannel can be connected to a plurality of microchannels. It will be apparent to the skilled artisan that by designing a layout for the master, and for the collapsible material cast on the master to form molded collapsible material, desired microchannel properties (collapsing versus non-collapsing) can be introduced into the molded collapsible material so that after microchannel collapse, a nanochannel can be connected to a plurality of microchannels, nanochannels or both microchannels and nanochannels, or that a microchannel can be connected to a plurality of microchannels, nanochannels or both microchannels and nanochannels.

In one embodiment, only the roof of the microchannel is capable of collapsing after it is bonded to a base. In another embodiment, the roof and/or the wall of the microchannel is capable of collapsing after it is bonded to a base.

In another embodiment, the base can comprise the floor and side walls of the microchannel, and the collapsible material can be laid across the top of the microchannel to form the roof of the microchannel.

Using nanofluidic or microfluidic devices comprising nanochannels, and/or nanochannel to microchannel transitions, produced by the methods provided herein, single molecules can be manipulated, the concentration of nanoscale particles can be determined, and nanoscale particles such as nucleic acid sequences can be detected. The method for fabricating a nanochannel can be used to fabricate a device for nucleic acid (e.g., DNA) elongation-based, nanofluidic concentration-based and surface enhanced Raman scattering (SERS) based-detection of nucleic acids.

Thus, in one embodiment, a method for detecting an analyte of interest is provided comprising the steps of:
  providing a nanochannel, wherein the nanochannel has a height ≤100 nm;
  introducing a fluidic sample suspected of containing the analyte of interest into the nanochannel;
  flowing the fluidic sample in the nanochannel; and
  detecting the presence or absence of the analyte in the nanochannel.

In one embodiment, the step of providing a nanochannel comprises the step of providing a nanofluidic or microfluidic device comprising the nanochannel.

In another embodiment, the analyte is a nucleic acid, the flowing step comprises the step of electrophoretically driving the nucleic acid in the nanochannel, thereby stretching the nucleic acid, and the detecting step comprises detecting the stretched nucleic acid.

In another embodiment, the detecting step comprises performing optical imaging.

In another embodiment, the detecting step comprises performing surface enhanced Raman scattering (SERS).

In another embodiment, the nanochannel has a height of 60-100 nm.

In another embodiment, the nanofluidic or microfluidic device additionally comprises a microchannel, and the nanochannel is fluidically connected to the microchannel by a microchannel to nanochannel transition.

In another embodiment, the step of flowing the fluidic sample in the nanochannel thereby concentrates the analyte at the microchannel to nanochannel transition.

The nanofluidic or microfluidic devices produced by the methods of the invention can be used as nanofilter devices to efficiently concentrate nanoparticles at the interface between microchannels and nanochannels that is created by the method for fabricating a nanochannel disclosed herein. Thus in one embodiment, a method is provided for concentrating nanoparticles.

In one embodiment, individual nucleic acid (e.g., DNA) molecules are imaged in solution as they passed through nanochannels fabricated on a microfluidic device (FIG. 4B and FIGS. 10 A-C). In the embodiment of the device illustrated in FIG. 4B and FIGS. 10 A-C, two large reservoirs (2 cm×5 mm×10 μm deep) are connected by nanochannels formed via the method for fabricating a nanochannel described above. When electrophoretically driven into the nanochannels, nucleic acid molecules such as DNA molecules will stretch to approximately 5 μm in length, which is approximately 25% of their full contour length.

The full contour length can be estimated using methods known in the art (Mannion J T, Reccius C H, Cross J D, Craighead H G (2006) Conformational Analysis of Single DNA Molecules Undergoing Entropically Induced Motion in Nanochannels. Biophys J 90: 4538-4545). Assuming that the root mean square end-to-end length of DNA, $L_z$, obeys Flory-Pincus scaling, it has been shown that $L_z=L(pw)^{1/3}d^{-2/3}$, where p is the persistence length, w is the molecule width, L is the contour length and d is the nanochannel width (Tegenfeldt J O, et al. (2004) The Dynamics of Genomic-Length DNA Molecules in 100-nm Channels. Proc Natl Acad Sci USA 101: 10979-10983). Using this relation, the nanochannel width can be extracted from the observed contour length of λ-DNA as it travels along the length of the nanochannel.

In another embodiment, a sample concentration ("nanofilter") device is provided that allows for rapid sample enrichment at a micro-/nanofluidic interface. FIG. 5A shows a schematic representation of one embodiment of the device, which was constructed by interfacing a single layer thickness master with one that was twice as thick. In other embodiments of the device, two or more masters of mismatched width can be interfaced.

As is shown in FIG. 5B, after casting the master in PDMS, the thin channel section forms two nanochannels (in this embodiment, 400 nm wide by 300 nm high) which was interfaced with a single microchannel (in this embodiment, 10 μm wide by 1.4 μm high).

A substance of interest in an aqueous solution can be introduced into the microchannel and caused to flow downstream electrophoretically through the application of an external electric field. FIG. 5C shows the accumulation of nanoparticles at the nanofluidic interfaces. By comparing the emitted florescent intensity in the concentration region with that in the normal flow using methods known in the art, the concentration of particles in a given amount of time can be estimated.

The concentration device described above can be used for Surface-Enhanced Raman Scattering (SERS) based detection of nucleic acids or other analytes or molecules of interest. Concentrated analytes of interest, e.g., molecules or nanoparticles, can be subjected to Surface Enhanced Raman Scattering (SERS) detection. SERS detection of nucleic acids, using an embodiment of a nanofluidic device comprising nanochannels made by the method of the invention, is shown in FIG. 6 and is described in more detail in Section 6.

Similar to the embodiments discussed above, the advantage of this embodiment of the nanofluidic concentrator device is that it can be fabricated simply by controlling the $a/h^2$ aspect ratio of the channels and allowing for elastomeric collapse without requiring additional processes. The concentrator device described above can be filled, via capillary force, with an aqueous solution of gold nanoparticles functionalized with nucleic acid sequences specific to a sequence of interest. After filling, the negatively charged gold nanoparticles can be concentrated at the entrance of the nanofluidic channel by applying an electric field using methods known in the art. To obtain the SERS signals from the resulting nanoparticle cluster, an excitation laser can be focused at the nanochannels interface and the emission spectrum recorded. The resulting SERS spectra can be collected for a range of desired concentration times.

5.3 Rapid Prototyping of Nanofluidic or Microfluidic Device

The methods for fabricating a nanochannel disclosed herein can be used as methods for the rapid prototyping of a variety of nanofluidic or microfluidic devices. Thus in one embodiment, methods for rapid prototyping of nanofluidic or microfluidic devices are provided.

Nanofluidic elements can be integrated with larger and more complex microfluidic structures that can facilitate high throughput or automated processing. In practice, this is often difficult to achieve because of mismatches in the fabrication technologies required. For example, nanofluidics may have been fabricated using electron-beam lithography and then the resulting structure aligned and assembled with another device fabricated using optical lithography. Mismatches between the materials compatible with each process and the difficulty in aligning microscale features with nanoscale ones, often makes this a difficult challenge. By changing an $a/h^2$ value at the interface, the method for fabricating a microchannel can be used for rapid prototyping of interfaced microfluidic and nanofluidic elements in a microfluidic device.

The following examples are offered by way of illustration and not by way of limitation.

6. EXAMPLES

6.1 Example 1

Method for Nanofluidic Device Prototyping Using Elastomeric Collapse 6.1.1 Introduction Nanofluidics represents a promising solution to problems in fields ranging from biomolecular analysis to optical property tuning. Recently a number of nanofluidic fabrication techniques have been introduced that exploit the deformability of elastomeric materials like polydimethylsiloxane (PDMS). These techniques are limited in the complexity of the devices which can be fabricated, being able to only create straight or irregular channels normal to the direction of an applied strain. This example demonstrates a method for fabricating a nanochannel that comprises the step of controlled collapsing of a microchannel structure. As is demonstrated, this method converts the easy to control vertical dimension of molded elastomer (e.g., molded PDMS elastomer) to the desired lateral dimension of a nanochannel. Using the method for fabricating a nanochannel, complex nanochannel structures were created as small as 60 nm.

This example also describes the design rules for determining the conditions under which nanochannel formation will occur. The applicability of the method to biomolecular analysis was demonstrated by showing DNA elongation in a nanochannel A technique for optofluidic surface enhanced Raman detection of nucleic acids was also developed.

This example demonstrates that under controllable conditions, the system can be made to collapse in such a way so as to leave nanofluidic channels as small as 60 nm from low resolution, but highly complex, photolithographic patterns. The material stiffness and geometric conditions which lead to this collapse are characterized along with how these parameters can be varied to obtain desired nanochannel sizes.

This method for fabricating a nanochannel can be used for rapid prototyping of complex nanofluidic systems. The usefulness of the method to practical nanofluidic system development was demonstrated by creating devices for DNA elongation, nanofluidic concentration and surface enhanced Raman scattering (SERS) based detection of nucleic acids using the technique.

6.1.2 Materials and Methods

Fabrication of PDMS Nanochannels

FIG. 1A shows a schematic of the method for fabricating a nanochannel. First, the desired pattern was made on a silicon wafer using standard photolithography processes. Negative photoresist SU-8 (Microchem, MA) 2000.5, 2002 and 2007 were used for different heights of the master in the range from 300 nm to 10 µm. The PDMS base to curing agent ratios were varied with 15:1, 10:1 and 5:1 by weight. After mixing the curing agent and elastomer base and degassing the mixture, it was cast onto the premade master and allowed to cure at 80° C. for 4 h. After the molded PDMS elastomer was removed from the master, it was bonded to a cover glass or a PDMS plain substrate by plasma oxidation for 30 s. Because the SU-8 film thickness could not be sufficiently well controlled to enable precisely characterization of the master thickness on the resulting nanochannels size, deposited aluminum layers were used as masters for these experiments. In this case, glass substrates (Borofloat wafer, Mark Optics, CA) were covered with a Shipley 1827 photoresist (Microchem, MA). Standard photolithography was used to pattern 100, 50, 20 and 10 µm wide features. Aluminum layers of 300, 400, 500, 700, 800, 900, 1000 nm thicknesses were deposited onto different glass wafers using an electron beam evaporator, CHA MARK 50 (CHA industry, CA). After deposition, the photoresist was removed using a lift-off process with Microposit 1165 (Microchem, MA) solvent over a 24 hour period. The final surface cleaning step was performed in a bath of acetone and isopropanol under gentle sonication.

Nanochannel Imaging and Characterization

To measure the cross-sectional dimensions of the nanochannels formed from this approach, fabricated PDMS-PDMS chips and PDMS-cover glass chips were frozen in liquid nitrogen, fractured with a chisel and mallet, coated with a Hummer V Au/Pd Sputtering System (Hummer, CA) and imaged with a scanning electron microscope (SEM, Zeiss Ultra/Supra, Germany). Examples of the fractured cross-sectional SEM images are shown in FIGS. 2A-D.

Preparation of Lambda Bacteriophage DNA for Elongation in Nanochannels

Lambda bacteriophage DNA (λ-DNA, New England Biolabs, MA) was labeled with the bis-intercalating dye, YOYO-1 (Molecular Probes, Eugene, Oreg.) at a nominal labeling ratio of 7.6:1 then introduced to the nanochannel, which has been filled with filtered 5× Tris Borate EDTA (TBE) buffer (Sigma, MO) at a concentration of 50 ng/ml. This buffer solution contains 3% (v/v) polyvinylpyrrolidone (Sigma, MO), a surfactant, to prevent the adhesion of the specimen to the surface of the nanochannels. 3% (v/v) β-mercaptoethanol (Sigma, MO) was also added to decrease the photobleaching effect. The sample solution was pipetted into one reservoir while the other was kept empty so as to induce capillary force filling of the nanochannels and to prevent air bubbles. After 10 minutes of capillary filling, the other reservoir was also filled with buffer solution. Inert gold wires contacting the solution in the reservoirs were used to apply an electric field over the nanochannels.

Preparation of DNA Hybridization Reaction and Raman Detection

For the Raman enhancers, 60 nm diameter gold colloid solutions were purchased from Nanocs (New York, N.Y.) and were diluted to a final concentration of 0.3 nM in 10 mM phosphate-buffered saline (PBS) buffer solution (0.6 M NaCl, pH 7.4). In this study, oligonucleotides which contain sequences specific to DENV-4 virus RNA were selected as the target analyte and were purchased from Operon Biotechnologies (Huntsville, Ala.). The capture probe for DENV-4a was 3' modified with a thiol-modifier containing C3 S-S functionality and had the following sequence: 5'-GAG GAA GCT GTA CTC CTG GTG GAA G C3 S-S-3' [SEQ ID NO: 1]. We analyzed the specificity of the SERS detection technique by conducting hybridization reaction using the target DNA of DENV-4a. The target probe was modified with Cy3 dye at the 5' end. The sequences of DENV-4a oligonucleotides were (Cy3) 5'-CTA GTC CTTCCACCAGGAGTACAGCTTCCTCCT GGC TTC G-3' [SEQ ID NO: 2]. The underlined portions of the target sequence are the complementary nucleotides to each capture probe. Details regarding the functionalization of the gold nanoparticles and DNA hybridization procedures can be found in Huh et al. (Huh Y S, Lowe A J, Strickland A D, Batt C A, Erickson D (2009) Surface-Enhanced Raman Scattering Based Ligase Detection Reaction. J Am Chem Soc 131: 2208-2213).

Briefly, to immobilize the probes, 300 nM of the thiolated capture DNA was added to a 0.3 nM gold colloid solution in PBS buffer solution for 6 h at room temperature, followed by a 1 h exposure to 30 µM carboxy-EG6-undecanethiol to prohibit non-specific binding. Following this, a centrifugation/resuspension cycle was carried out at 10 000 rpm for 30 min repeated three times for the removal of excess reagents. The gold NPs immobilized capture probe were resuspended to the final concentration of 3 nM capture probe in the hybridization buffer. Cy3-labeled target DNA in PBS buffer solution was added to gold nanoparticles functionalized with capture probes. After 12 h, the excess target probes were removed by centrifugation and repeated three times at 10 000 rpm for 30 min. Then, the gold nanoparticles were resuspended in PBS buffer solution and were introduced through the inlet port of the nanofluidic device by applying electric field of 40 V/cm. Raman spectra were measured with an in Via Raman microscope spectrometer (UK) coupled to a Leica microscope (Germany). The diode laser used here had an excitation wavelength of 785 nm and operated at approximately 5 mW power. Wave-number ranges from 1000 $cm^{-1}$ to 1800 $cm^{-1}$ were examined here. A 50× long working distance objective lens was used with a spot size of 2 µm.

6.1.3 Results

Nanochannel Formation and Characterization

One exemplary embodiment of the method for nanochannel formation is shown schematically in FIGS. 1A-B. Details of the fabrication process are provided in the methods section, however, briefly the desired PDMS microchannels are obtained using patterned metal or SU-8 masters and traditional soft lithography processes (McDonald J C, et al. (2000) Fabrication of microfluidic systems in poly(dimethylsiloxane). Electrophoresis 21: 27-40). Under the proper conditions (characterized below) when placed in conformal contact the microchannel will collapse and the roof will bond to the lower substrate. By controlling the thickness of the master, the width of the channel feature and the elasticity of the PDMS with various elastomer/elastomer base ratios, we are able to create a large range of nanochannel sizes, shapes and fluidic layouts (FIGS. 7A-D).

To measure the dimensions of the fabricated devices, scanning electron microscopy (SEM) image analysis of fractured nanochannels cross-section was performed (see Materials and Methods section for details). Sample cross-sectional images of 4 different types of nanochannel systems are shown in FIGS. 2A-D, namely (A) PDMS/PDMS (B) PDMS/Glass (C) PDMS/PDMS with 50 kPa compressive pressure applied from above and (D) PDMS/Glass also with the external applied pressure. Most nanochannels fabricated by this approach had a triangular cross-section (as in FIGS. 2A and 2B), the exception being those subject to a compressive force which were generally semi-circular (FIGS. 2C and 2D). The applied compressive stress also served to shrink the width and height of the nanochannel. The PDMS/PDMS channels shown in FIGS. 2A and 2C were fabricated under the same master height (700 nm) and elastomer/base conditions (10:1). The uncompressed channel has a cross section with the dimension of 380 nm (width) by 300 nm (height). When the compressive stress is applied the channel height (normal to the pressure direction) is shown to shrink by approximately 5 fold to 60 nm and the channel width reduced to 200 nm The compressed nanochannels were formed right after the oxidizing treatment and thus it is believed that this process should be irreversible so that the final dimension of the nanochannels remains dimensionally stable. As can also be seen in FIGS. 2A-D, in both the compressed and uncompressed cases, the use of a stiffer lower substrate (glass vs. PDMS) tended to result in channels with larger widths and heights.

To determine the dependence of mater height and material elasticity on the formed nanochannel width, a number of experiments were performed using masters with a range of heights (300, 400, 500, 700, 800, 900 and 1000 nm) and PDMS with different elastomer/base ratios (5:1, 10:1 and 15:1). The width and height of the nanochannel is smaller for shorter master heights and greater elastomer:base ratios (or equivalently greater elasticity (Wilder E A, Guo S, Lin-Gibson S, Fasolka M J, Stafford C M (2006) Measuring the Modulus of Soft Polymer Networks via a Buckling-Based Metrology. Macromolecules 39: 4138-4143)). The unsagged length of the PDMS (which in this case represents the final nanochannel width, L) is proportional to the elastic modulus, E, times the square of the master height, h, or $L \propto Eh^2$ (Huang Y Y, et al. (2005) Stamp Collapse in Soft Lithography. Langmuir 21: 8058-8068) and Zhou et al. (Zhou W, et al. (2005) Mechanism for stamp collapse in soft lithography. Appl Phys Lett 87: 251925-3). As can be seen in FIG. 3A, the results agree with this quadratic relation. According to Wilder et al. (Wilder E A, Guo S, Lin-Gibson S, Fasolka M J, Stafford C M (2006) Measuring the Modulus of Soft Polymer Networks via a Buckling-Based Metrology. Macromolecules 39: 4138-4143), 5:1 PDMS has larger elastic modulus (~2.6 MPa) than that of 10:1 PDMS (~1.6 MPa). Using a non-linear least-squares algorithm to fit both curves from FIG. 3A a ratio of elastic moduli for 5:1 and 10:1 PDMS of 1.58 was obtained, which is similar to that obtained from Wilder et al.'s results (1.63) (Wilder E A, Guo S, Lin-Gibson S, Fasolka M J, Stafford C M (2006) Measuring the Modulus of Soft Polymer Networks via a Buckling-Based Metrology. Macromolecules 39: 4138-4143). Although the oxidation of the PDMS surface resulted in more stable formation of nanochannels, it did not affect the final dimension of the formed nanochannels (FIGS. 8A-B).

There were two cases in which nanochannels formation was not successful: when the formed microchannel failed to collapse and when the collapse resulted in complete sealing or annihilation of the desired structure. To quantify the conditions that resulted in high device yields, experiments were performed under different fabrication conditions to obtain a "nanochannel formation success rate" which is defined as the percentage of channels in which stable roof collapse was observed (see Table 1 for complete experimental results).

TABLE 1

Success rate of nanochannel formation under various conditions including: master width, master height, with and without plasma oxidation, and different elastomer: base ratios.

| Master Width (μm) | Master Height (nm) | Non-Oxidized PDMS Elastomer:Elastomer base ratios | | | Oxidized PDMS | | |
|---|---|---|---|---|---|---|---|
| | | 5:1 | 10:1 | 15:1 | 5:1 | 10:1 | 15:1 |
| 10 | 300 | 25.6 ± 5.3 | 43.2 ± 7.2 | A | 91.3 ± 8.2 | 92.6 ± 7.8 | A |
| | 400 | 19.4 ± 3.1 | 39.2 ± 4.2 | 87.8 ± 3.2 | 31.7 ± 6.2 | 65.8 ± 4.7 | A |
| | 500 | 15.7 ± 3.2 | 32.4 ± 3.8 | 77.4 ± 4.3 | 53.3 ± 7.7 | 61.2 ± 5.4 | 83.6 ± 3.2 |
| | 700 | 7.3 ± 2.3 | 31 ± 4.5 | 18.4 ± 4.9 | 43.7 ± 8.7 | 52.2 ± 7.6 | 45.3 ± 6.3 |
| | 800 | 2.5 ± 1.1 | 7.3 ± 2.3 | 8.2 ± 2.1 | 6.7 ± 2.6 | 9.8 ± 3.4 | 9.3 ± 3.7 |
| | 900 | N | 2.7 ± 1.2 | 7.5 ± 2.5 | 4.2 ± 1.9 | 6.5 ± 2.8 | 8.6 ± 2.6 |
| | 1000 | N | 2.5 ± 0.7 | 5.2 ± 3.1 | 3.6 ± 0.8 | 5.5 ± 2.1 | 7.8 ± 3.8 |
| 20 | 300 | 72.3 ± 5.2 | 94.5 ± 5.7 | A | 95.7 ± 5.2 | A | A |
| | 400 | 39.7 ± 4.6 | 48.9 ± 6.4 | A | 81.4 ± 3.9 | 94.2 ± 6.9 | A |
| | 500 | 33.4 ± 5.1 | 40.3 ± 6.7 | 94.3 ± 6.4 | 62.5 ± 4.7 | 71.4 ± 4.6 | A |
| | 700 | 15.3 ± 3.3 | 28.7 ± 5.6 | 85.3 ± 7.5 | 58.9 ± 3.7 | 65.6 ± 6.5 | 95.3 ± 5.4 |
| | 800 | 7.4 ± 2.5 | 9.5 ± 3.9 | 35.7 ± 4.8 | 10.8 ± 2.3 | 12.7 ± 4.5 | 55.3 ± 7.4 |
| | 900 | N | 3.7 ± 1.7 | 21.2 ± 4.5 | 8.6 ± 2.3 | 9.5 ± 3.2 | 45.5 ± 5.3 |
| | 1000 | N | 2.5 ± 0.5 | 8.7 ± 3.3 | 7.1 ± 1.8 | 8.2 ± 2.6 | 9.5 ± 2.9 |
| 50 | 300 | 95.4 ± 5.7 | A | A | A | A | A |
| | 400 | 94.7 ± 6.2 | A | A | A | A | A |
| | 500 | 63.7 ± 4.2 | 94.5 ± 6.7 | A | 94.1 ± 6.5 | 94.9 ± 6.3 | A |
| | 700 | 23.4 ± 5.9 | 44.8 ± 5.7 | A | 71.4 ± 5.3 | 82.2 ± 4.5 | A |
| | 800 | 7.7 ± 2.1 | 19.3 ± 3.7 | 95 ± 5.3 | 28.7 ± 6.3 | 45.7 ± 4.6 | A |

TABLE 1-continued

Success rate of nanochannel formation under various conditions including: master width, master height, with and without plasma oxidation, and different elastomer: base ratios.

| Master Width (μm) | Master Height (nm) | Non-Oxidized PDMS | | | Oxidized PDMS | | |
|---|---|---|---|---|---|---|---|
| | | 5:1 | 10:1 | 15:1 | 5:1 | 10:1 | 15:1 |
| | 900 | 5.1 ± 1.5 | 11.7 ± 2.3 | 83.1 ± 6.7 | 23.4 ± 4.1 | 25.7 ± 5.3 | 96.5 ± 5.7 |
| | 1000 | N | 9.3 ± 2.3 | 69.5 ± 5.4 | 21.5 ± 4.5 | 15.3 ± 3.2 | 85.3 ± 6.2 |
| 100 | 300 | 94.5 ± 7.4 | A | A | A | A | A |
| | 400 | 94.1 ± 6.3 | A | A | A | A | A |
| | 500 | 93.7 ± 7.4 | A | A | 94.5 ± 6.7 | A | A |
| | 700 | 75.4 ± 5.9 | 95.5 ± 5.3 | A | 92.4 ± 5.4 | 95.1 ± 6.6 | A |
| | 800 | 39.2 ± 4.8 | 64.3 ± 4.7 | A | 92.1 ± 4.6 | 94.6 ± 5.4 | A |
| | 900 | 26.3 ± 5.7 | 40.2 ± 4.2 | 96.7 | 70.3 ± 6.3 | 83.4 ± 4.3 | A |
| | 1000 | 7.5 ± 2.4 | 27.3 ± 6.7 | 94.2 | 45.7 ± 4.7 | 58.4 ± 5.9 | A |

A and N represent "annihilation" and "NO-collapse," respectively.

In FIG. 3B this parameter is plotted as a function of the original master's width, a, divided by its height, h, squared. The $a/h^2$ parameter is proportional to the work required to achieve contact between the molded PDMS elastomer and the lower substrate according to Huang et al. (Huang Y Y, et al. (2005) Stamp Collapse in Soft Lithography. Langmuir 21: 8058-8068). As with the above, in addition to the geometric parameters, other variables including the surface energy of the molded PDMS elastomer and the plain substrate (i.e. with and without plasma oxidation) and the elastomer: base ratio can also be considered. In all these experiments, the formation of nanochannels was assessed using SEM and optical microscopy.

On the basis of these results, four regions could be identified: a no-collapse region for weak adhesion (<10% success rate of nanochannel formation), a metastable collapse region for intermediate adhesion (<90% success rate of nanochannel formation), a stable, high yield, collapse region for strong adhesion (>90% collapse), and an annihilation region in which the nanochannels disappeared (FIG. 3C). As can be seen in FIG. 3B, for all cases as the work of adhesion increased the nanochannel formation success rate also increased. Successful nanochannel formation of 5:1 and 10:1 PDMS remained below 10% yield until approximately $a/h^2=0.1$. Above $a/h^2=0.2$, the success rate of nanochannel formation was around 90%. The formed nanochannels started to disappear (annihilation) above $a/h^2=0.3$ owing to complete collapse of the channel. As can also be seen, greater nanochannel formation rates were generally observed when molded PDMS elastomers with greater elasticity were used (elastomer: base ratios of 15:1 and 10:1) than with the stiffer material. This is because the deformation energy of the molded PDMS elastomer increases as the stiffness of PDMS decreases. Similarly, owing to the higher surface energy of the molded PDMS elastomer and the substrate, the oxidized molded PDMS elastomer resulted in a higher success rate of nanochannel formation. Based on these experimental results, we used master geometries ranging from 500 nm to 700 nm in height, from 10 μm to 100 μm in width and from 5:1 to 10:1 oxidized PDMS for the remainder of the devices used in this study.

Nanofluidic and Single Molecule Manipulation

To test the fluidic continuity of the formed nanochannels, they were filled with a solution of 100 μM Rhodamine B in 50:50 isopropanol/water and imaged using an optical microscope (Olympus IX-70 microscope, Olympus, Japan). As is shown in FIGS. 4A-B, in these experiments straight nanochannels were used as well as a number of more complicated designs (FIGS. 9A-C). This demonstrates the ability of the technique to create nanofluidic systems with arbitrary layouts using low-resolution optical lithography.

To demonstrate the practical application of these devices to single molecule analysis, individual DNA molecules were imaged in solution as they passed through the nanochannels (see FIG. 4B and FIGS. 10 A-C). The device used here had two large reservoirs (2 cm×5 mm×10 μm deep) connected by nanochannels formed via the collapsing method described above. When electrophoretic ally driven into the nanochannels, the DNA molecules stretched to approximately 5 μm in length, which is approximately 25% of their full contour length. The full contour length of 48.5 kbp λ-DNA can be calculated from the basepair spacing of 0.34 nm and the additional 30% increase cased by intercalation of the YOYO-1 dye (Mannion J T, Reccius C H, Cross J D, Craighead H G (2006) Conformational Analysis of Single DNA Molecules Undergoing Entropically Induced Motion in Nanochannels. Biophys J 90: 4538-4545) to be approximate 20 μm. Assuming that the root mean square end-to-end length of DNA, $L_z$, obeys Flory-Pincus scaling, it has been shown that $L_z=L(pw)^{1/3} d^{-2/3}$, where p is the persistence length, w is the molecule width, L is the contour length and d is the nanochannel width (Tegenfeldt J O, et al. (2004) The Dynamics of Genomic-Length DNA Molecules in 100-nm Channels. Proc Natl Acad Sci USA 101: 10979-10983). Using this relation, the nanochannel width can be extracted from the observed contour length of λ-DNA as it travels along the length of the nanochannel.

FIG. 4B illustrates the motion of a DNA molecule under an electric field in the nanochannels at three different locations. As is shown in these images, the stretched length did not vary significantly along the length of the channel, suggesting that the formed channels are both continuous and uniform along their length. Based on the above theory, the observed length of 5 μm indicates that the confined nanochannel width is approximately 200 nm in one axis (see FIG. 10 B). This is consistent with the observed 8 μm contour length observed by Tegenfeldt et al. (Tegenfeldt J O, et al. (2004) The Dynamics of Genomic-Length DNA Molecules in 100-nm Channels. Proc Natl Acad Sci USA 101: 10979-10983) for 100 nm channels.

Interfacing Micro- and Nanofluidic Structures and Demonstration of a Concentration Device Nanofluidic elements (which enable single molecule manipulations such as that shown above) can be integrated with larger and more complex microfluidic structures which can facilitate high throughput or automated processing. In practice, this is often difficult to achieve because of mismatches in the fabrication technologies required. For example, nanofluidics may have been fabricated using electron-beam lithography and then the resulting structure aligned and assembled with another device fabricated using optical lithography. Mismatches between the materials compatible with each process and the difficulty in aligning microscale features with nanoscale ones, often makes this a difficult challenge. By simply changing an $a/h^2$ value at the interface, the technique can be used for rapid prototyping of interfaced microfluidic and nanofluidic elements in a microfluidic device.

This was demonstrated by developing a sample concentration device that allows for rapid sample enrichment at a micro-/nanofluidic interface. FIG. 5A shows a schematic representation of the device which was constructed by interfacing a single layer thickness master with one that was twice as thick. Equivalent results could be achieved by using mismatched widths as well. As is shown in FIG. 5B, after casting the master in PDMS, the thin channel section formed two nanochannels (400 nm wide by 300 nm high) which was interfaced with a single microchannel (10 µm wide by 1.4 µm high). To characterize the concentration capability of this device, negatively charged fluorescent polystyrene nanoparticles with diameters of 700 nm and 45 nm in an aqueous solution were introduced into the microchannel and caused to flow downstream electrophoretically through the application of an external electric field with a strength of 40 V/cm. FIG. 5C shows the accumulation of 700 nm nanoparticles at the nanofluidic interface over the course of 60 seconds. By comparing the emitted florescent intensity in the concentration region with that in the normal flow, we estimate at least a 30 fold concentration of the particles in 1 minute. Concentration of 45 nm nanoparticles at the interface (see FIG. 10 D) was also demonstrated.

Surface Enhanced Raman Spectroscopy (SERS) Based Detection of Nucleic Acids

To demonstrate the use of the approach to biomolecular detection, the concentration device described above was used for SERS based detection of nucleic acids. In recent studies (Huh Y S, Lowe A J, Strickland A D, Batt C A, Erickson D (2009) Surface-Enhanced Raman Scattering Based Ligase Detection Reaction. J Am Chem Soc 131: 2208-2213; Graham D, Thompson D G, Smith W E, Faulds K (2008) Control of enhanced Raman scattering using a DNA-based assembly process of dye-coded nanoparticles. Nature Nanotech 3: 548-551; Piorek B D, et al. (2007) Free-surface microfluidic control of surface-enhanced Raman spectroscopy for the optimized detection of airborne molecules. Proc Natl Acad Sci USA 104: 18898-18901) metal colloid aggregation and concentration have been shown to significantly enhance the sensitivity and reproducibility of SERS based measurements. Chou et al. (Chou I H, et al. (2008) Nanofluidic Biosensing for β-Amyloid Detection Using Surface Enhanced Raman Spectroscopy. Nano Lett 8: 1729-1735) for example recently reported a device that trapped metal nanoparticles at a microchannel-nanochannel junction, which has the coupled effect of both increasing the intensity of the surface plasmon field (through multi-particle interactions) and the number of local emitters ultimately yielding an enhanced limit of detection for solution phase β-amyloids. As another example, Choi et al. investigated an optofluidic compact disc (CD) platform (Choi D, Kang T, Cho H, Choi Y, Lee L P (2009) Additional amplifications of SERS via an optofluidic CD-based platform. Lab Chip 9: 239-243). The Choi et al. device allows the accumulation of target molecules and SERS enhancers via centrifugal force.

The applicability of the rapid prototyping technique to biomolecular sensing was demonstrated here through the development of a SERS-based detection technique enhanced by the nanofluidic concentrator device described above. Similar to the embodiments discussed above, the advantage of this embodiment of the nanofluidic concentrator device was that it could be fabricated simply by controlling the $a/h^2$ aspect ratio of the channels and allowing for elastomeric collapse without requiring additional processes. The device was used to detect nucleic acid sequences associated with Dengue virus serotype 4 (DENV-4). Dengue virus is an acute febrile viral disease characterized by sudden fever and onset, and there are four different serotypes (DENY-1-4) (Franz A W E, et al. (2006) Engineering RNA interference-based resistance to dengue virus type 2 in genetically modified Aedes aegypti. Proc Natl Acad Sci USA 103: 4198-4203).

In this experiment, the same micro-/nanofluidic concentrator device described above was filled, via capillary force, with an aqueous solution of gold nanoparticles functionalized with nucleic acid sequences specific to DENV-4 (see Methods section above for details). After filling, the negatively charged gold nanoparticles were concentrated at the entrance of the nanofluidic channel by applying the same 40 V/cm electric field used above for as long as 60 s. To obtain the SERS signals from the resulting nanoparticle cluster, the excitation laser was focused at the nanochannels interface and the emission spectrum recorded between a wave-number range of 1000 $cm^{-1}$ to 1800 $cm^{-1}$ using a 15 second integration time.

The resulting SERS spectra of Cy3-labeled DENV-4a is shown in FIG. 6, collected for concentration times ranging from 5 s to 60 s. As seen in FIG. 6, the results show that the correct spectroscopic fingerprints corresponded to Cy3-labeled dye (Cao Y C, Jin R, Mirkin C A (2002) Nanoparticles with Raman Spectroscopic Fingerprints for DNA and RNA Detection. Science 297: 1536-1540) and that the intensity increases with the accumulation time, as expected.

6.1.4 Discussion

PDMS is a popular material for rapid prototyping of microfluidics, owing to its easy patterning, optical transparency and flexibility (Wu H, Odom T W, Chiu D T, Whitesides G M (2003) Fabrication of Complex Three-Dimensional Microchannel Systems in PDMS. J Am Chem Soc 125: 554-559; Genzer J, Efimenko K (2000) Creating Long-Lived Superhydrophobic Polymer Surfaces Through Mechanically Assembled Monolayers. Science 290: 2130-2133; Diaz-Quijada G A, Wayner D D M (2004) A Simple Approach to Micropatterning and Surface Modification of Poly(dimethylsiloxane). Langmuir 20: 9607-9611; Wilbur J L, Kim E, Younan X, Whitesides G M (1995) Lithographic molding: A convenient route to structures with sub-micrometer dimensions. Adv Mater 7: 649-652). This example demonstrates a method for the creation of nanochannels and nanofluidic systems based on controlled elastomeric (PDMS) collapse. The method combines the dimensional range and network complexity that can be obtained from high-end nanofabrication technique with the simplicity of recently demonstrated non-lithographic approaches nanofluidic rapid prototyping devices.

To achieve nanofluidic systems embedded in a PDMS microfluidic format, a variety of methods have been reported including reversible bonding between glass and PDMS (Kim S M, Burns M A, Hasselbrink E F (2006) Electrokinetic Protein Preconcentration Using a Simple Glass/Poly(dimethylsiloxane) Microfluidic Chip. Anal Chem 78: 4779-4785), the junction gap breakdown of PDMS at high voltages (Lee J H, Chung S, Kim S J, Han J (2007) Poly(dimethylsiloxane)-Based Protein Preconcentration Using a Nanogap Generated by Junction Gap Breakdown. Anal Chem 79: 6868-6873), and nanocapillary array integration (Kim S J, Han J (2008) Self-Sealed Vertical Polymeric Nanoporous-Junctions for High-Throughput Nanofluidic Applications. Anal Chem 80: 3507-3511). However, these methods led to relatively poor coupling between microstructures and nanoscale structures. The method demonstrated in this example greatly facilitates this. By building some structures with an $a/h^2$ value in the range in which nanochannels formation is highly likely and others where this value is in the range where collapse will not happen (leaving behind a microchannel) an interface is enabled between the two types of channels.

In summary, while generally PDMS has been considered as a polymeric platform for microscale structures, the method for fabricating nanochannels demonstrated in this example expands the use of PDMS and other similar collapsible materials (e.g., polymers or other elastomers) from micro to nanoscale platform, enabling rapid prototyping of a wide range of geometries. Another advantageous feature of the method for fabricating nanochannels is its design flexibility. Because the nanochannel layout matches that of its corresponding master, nanochannels can be formed into complex patterns (so long as the master holds a looped curve). Since the master can be freely designed with basic, low resolution photolithography, a major advantage of this method is that it affords a large degree of freedom in designing functional nanofluidic structures, as opposed to previous approaches which only enable straight lines. This form of nanofabrication can thus strongly facilitate the rapid prototyping of a variety of nanofluidic devices.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for fabricating a nanochannel comprising:
   (a) providing a microchannel comprising a roof, a wall, and a bottom, the microchannel having a feature that promotes a desired frequency of microchannel collapse; and
   (b) controlling collapse of the microchannel to create a nanochannel defined or enclosed by a portion of the collapsed roof, the wall, and a portion of the bottom of the microchannel.

2. The method of claim 1 wherein the step of controlling collapse of the microchannel comprises controlling collapse of the roof of the microchannel.

3. The method of claim 1 wherein the microchannel comprises a collapsible material.

4. The method of claim 3 wherein the roof of the microchannel comprises the collapsible material.

5. The method of claim 3 wherein the collapsible material is an elastomer.

6. The method of claim 5 wherein the elastomer is polydimethylsiloxane (PDMS).

7. The method of claim 1 wherein a height of the nanochannel is ≤100 nm.

8. The method of claim 1 wherein a height of the nanochannel is 60-100 nm.

9. The method of claim 1 wherein an $a/h^2$ value of the microchannel is in a range from 0.2 to 0.3 in which roof collapse is likely, where a is an original master width and h is an original master height.

10. The method of claim 1 wherein the step of controlling collapse of the microchannel comprises the step of applying a compressive force to the microchannel.

11. The method of claim 1 wherein the step of providing the microchannel comprises the steps of:
   providing a molded or patterned collapsible material, the molded or patterned collapsible material having a geometric feature, a stiffness feature or a flexibility feature that promotes a desired frequency of microchannel collapse;
   providing a base; and
   bonding the molded or patterned collapsible material to the base, thereby forming the microchannel.

12. The method of claim 11 wherein the base is elastomer, polymer, glass or silicon.

13. The method of claim 11 wherein the molded or patterned collapsible material is an elastomer.

14. The method of claim 11 wherein the step of providing the molded or patterned collapsible material comprises the step of nano imprinting or micro imprinting collapsible material or precursor collapsible material to form the molded or patterned collapsible material.

15. The method of claim 11 wherein the step of providing the molded or patterned collapsible material comprises the steps of:
   providing a master, wherein the master is configured to have a geometric condition that promotes a desired frequency of microchannel collapse;
   forming the molded or patterned collapsible material on the master, the molded or patterned collapsible material having a material stiffness that promotes a desired frequency of microchannel collapse; and
   removing the molded or patterned collapsible material from the master.

16. The method of claim 15 wherein the step of forming the molded or patterned collapsible material on the master comprises the step of casting or molding precursor collapsible material on the master.

17. The method of claim 16 comprising, after the step of casting or molding precursor collapsible material on the master, the step of curing the precursor collapsible material to form the molded or patterned collapsible material.

18. The method of claim 15 wherein the master is a sacrificial material.

19. The method of claim 15 wherein the master comprises a photoresist or a deposited layer of metal.

20. The method of claim 15 wherein the master comprises two or more interfaced masters of mismatched width.

21. The method of claim 15 wherein the step of providing a master comprises the step of making the master from a pattern, wherein the pattern is configured to have a geometric condition that promotes a desired frequency of microchannel collapse and wherein the pattern has a desired nanochannel or microchannel layout.

22. The method of claim 21 wherein the pattern is on a silicon wafer.

23. A method for fabricating a microchannel to nanochannel transition comprising:
(a) providing a first microchannel and a second microchannel, wherein at least the first microchannel comprises a roof, a wall, and a bottom, and has a feature that promotes a desired frequency of microchannel collapse; and
(b) controlling collapse of the first and second microchannels whereby the first microchannel collapses to create a nanochannel defined or enclosed by a portion of the collapsed roof, the wall, and a portion of the bottom of the first microchannel, and the second microchannel does not collapse or collapses to form a smaller microchannel, whereby the nanochannel and the microchannel are operatively connected after the collapse.

24. The method of claim 23 wherein the first microchannel or the second microchannel are connected to one or more microchannels.

25. A method for fabricating a nanofluidic or microfluidic device comprising the step of fabricating a nanochannel, wherein the step of fabricating the nanochannel comprises:
(a) providing a microchannel comprising a roof, a wall, and a bottom, the microchannel having a feature that promotes a desired frequency of microchannel collapse; and
(b) controlling collapse of the microchannel to create a nanochannel defined or enclosed by a portion of the collapsed roof, the wall, and a portion of the bottom of the microchannel.

26. The method of claim 25 wherein an $a/h^2$ value of the microchannel is in a range from 0.2 to 0.3 in which roof collapse is likely and wherein a nanochannel is produced, where a is an original master width and h is an original master height.

27. The method of claim 25 further comprising the step of fabricating a microchannel on the device, wherein the step of fabricating the microchannel comprises:
providing a second microchannel; and
controlling collapse of the second microchannel wherein the microchannel does not collapse or collapses to form a smaller microchannel.

28. The method of claim 27 wherein an $a/h^2$ value is in range than 0.1 in which roof collapse is unlikely and wherein a microchannel is produced, where a equals an original master width and h equals an original master height.

29. A method for prototyping a nanofluidic or microfluidic device comprising the step of fabricating a nanochannel using the method of claim 1.

* * * * *